(12) United States Patent
Domb

(10) Patent No.: US 8,575,092 B2
(45) Date of Patent: Nov. 5, 2013

(54) GELLING HYDROPHOBIC INJECTABLE POLYMER COMPOSITIONS

(75) Inventor: Abraham Jackob Domb, Efrat (IL)

(73) Assignee: Efrat Biopolymers Ltd., Efrat (IL)

( * ) Notice: Subject to any disclaimer, the term of this patent is extended or adjusted under 35 U.S.C. 154(b) by 1210 days.

(21) Appl. No.: 11/992,669

(22) PCT Filed: Sep. 27, 2006

(86) PCT No.: PCT/IB2006/003540
§ 371 (c)(1),
(2), (4) Date: Mar. 27, 2008

(87) PCT Pub. No.: WO2007/110694
PCT Pub. Date: Oct. 4, 2007

(65) Prior Publication Data
US 2009/0111732 A1 Apr. 30, 2009

Related U.S. Application Data

(60) Provisional application No. 60/720,840, filed on Sep. 27, 2005.

(51) Int. Cl.
*A61K 31/00* (2006.01)
*A61K 47/30* (2006.01)
*C08G 63/06* (2006.01)
*C08G 63/00* (2006.01)

(52) U.S. Cl.
USPC ........... 514/2.1; 514/772.3; 514/44; 528/361; 528/271

(58) Field of Classification Search
USPC ....................... 514/2, 772.3, 44; 528/271, 361
See application file for complete search history.

(56) References Cited

U.S. PATENT DOCUMENTS

2009/0111732 A1   4/2009  Domb

FOREIGN PATENT DOCUMENTS

| EP | 0952171 | 10/1999 |
|---|---|---|
| WO | WO 98/02171 | 1/1998 |
| WO | WO 02/44232 | 6/2002 |
| WO | WO 2005/079861 | * 9/2005 |
| WO | WO 2007/110694 | 10/2007 |

OTHER PUBLICATIONS

Domb et al. Procedings of the 8th Polymer for Advanced Technologies International Symposium Sep. 13-16, 2005.*
International Preliminary Report on Patentability Dated Jul. 17, 2008 From the International Bureau of WIPO Re.: Application No. PCT/IB2006/003540.
Communication Pursuant to Article 94(3) EPC Dated Aug. 18, 2009 From the European Patent Office Re.: Application No. 06849434.3.
International Search Report Dated Jun. 12, 2008 From the International Searching Authority Re.: Application No. PCT/IB2006/003540.
Written Opinion Dated Jun. 12, 2008 From the International Searching Authority Re.: Application No. PCT/IB2006/003540.
Krasko et al. "Poly(Ester Anhydride)s Prepared by the Insertion of Ricinoleic Acid Into Poly(Sebacic Acid)" Journal of Polymer Science, Part A: Polymer Chemistry, XP002482307, 41(8): 1059-1069, Feb. 21, 2003. Tabel 1, p. 1063, col. 2, § 1, p. 1066, col. 2, § 2, fig.7, p. 1067, col. 1, § 1.
Leong et al. "Polyanhydrides for Controlled Release of Bioactive Materials", Biomaterials, XP002204894, 7(5): 364-371, Sep. 1, 1986. Abstract, p. 365, col. l, § 1.
Shikanov et al. "Poly(Sebacic Acid-Co-Ricinoleic Acid) Biodegradable Carrier for Paclitaxel: In Vitro Release and In Vivo Toxicity", Journal of Biomedical Materials Research, Part A, XP002482308, 69(1): 47-54, Apr. 1, 2004. p. 48, col. 1, § 3, p. 49, col. 1, § 2,p. 53, col.2, § 2.
Response Dated Dec. 16, 2009 to Communication Pursuant to Article 94(3) EPC of Aug. 18, 2009 From the European Patent Office Re.: Application No. 06849434.3.
Examiner's Report Dated Feb. 8, 2011 From the Australian Government, IP Australia Re. Application No. 2006341116.
Office Action Dated Dec. 1, 2011 From the Israel Patent Office Re. Application No. 190486 and its Translation Into English.
Patent Examination Report Dated Jul. 12, 2012 From the Australian Government, IP Australia Re. Application No. 2006341116.
Translation of Notice of Reason for Rejection Dated May 15, 2012 From the Japanese Patent Office Re. Application No. 2008-532902.
Krasko et al. "Hydrolytic Degradation of Ricinoleic-Sebacic-Ester-Anhydride Copolymers", Biomacromolecules, 6(4): 1877-1884, 2005.
Shikanov et al. "Poly(Sebacic Acid-Co-Ricinoleic Acid) Biodegradable Carrier for Paclitaxcl: In Vitro Release and In Vivo Toxicity", Journal of Biomedical Materials Research, Part A, XP002482308, 69(1): 47-54, Apr. 1, 2004. p. 48, col. 1, § 3, p. 49, col. 1, § 2, p. 53, col. 2, § 2.

* cited by examiner

*Primary Examiner* — Shirley V Gembeh
(74) *Attorney, Agent, or Firm* — Pabst Patent Group LLP

(57) ABSTRACT

Biodegradable carriers synthesized from ricinoleic acid oligoesters and aliphatic molecules having at least one carboxylic acid and at least one hydroxy or carboxylic acid group that are liquids or pastes at temperatures below 37° C. and methods of making and using thereof are described herein. The polymers described herein significantly increase their viscosity upon immersion in aqueous medium. These polymers can be used as hydrophobic biomedical sealants, temporary barriers to prevent adhesions, such as organ to organ adhesion, cell supports, carriers for drug delivery, and coatings on implantable medical devices, such as stents. The polymers made from ricinoleic acid oligoesters are less viscous and easier to inject compared to polymers of similar composition and molecular weight prepared from ricinoleic acid monomers, possess a higher molecular weight, retain an incorporated drug for longer periods, and degrade into soft degradation products at a slower rate compared with polymers synthesized from ricinoleic acid monomers. Pharmaceutically active agents can be incorporated into the liquid or pastes without the use of organic solvents.

23 Claims, 9 Drawing Sheets
(4 of 9 Drawing Sheet(s) Filed in Color)

GELLING HYDROPHOBIC INJECTABLE POLYMER COMPOSITIONS

RELATED APPLICATIONS

This Application is a National Phase of PCT Patent Application No. PCT/IB2006/003540 having International Filing Date of Sep. 27, 2006, which claims the benefit of U.S. Provisional Patent Application No. 60/720,840 filed on Sep. 27, 2005. The contents of the above Applications are all incorporated herein by reference.

FIELD OF THE INVENTION

This invention is generally in the field of gelling hydrophobic polymer compositions for the controlled release of pharmaceutically active agents.

BACKGROUND OF THE INVENTION

In situ depot forming systems for parenteral controlled drug delivery are typically in the form of liquids or pastes having a wide range of viscosities. Such systems usually contain a biodegradable carrier dissolved or dispersed in a solvent/cosolvent system, while the drug is either dispersed or dissolved in the liquid phase of the delivery system. Upon subcutaneous or intramuscular injection, a solid depot is formed at the site of injection. The administration of such a system is far less invasive and costly than the surgical procedures which are often required for implantation. Different in situ depot forming systems have recently been reviewed and classified into different categories according to the depot forming mechanism (Hatefi et al., *J. Control. Release* 80(1-3):9-28 (2002)).

In situ precipitation systems formed with polylactide-co-glycolide ("PLGA") copolymers have gained the most attention in recent years because of the regulatory approval of specific products, such as Eligard®, which uses the Atrigel® technology for long-term delivery of leuprolide acetate. Eligard® is marketed by Atrix Lab (now QLT). N-methyl-2-pyrrolidone (NMP) is the organic solvent used in this particular formulation. Other organic solvents such as propylene glycol, dimethyl sulfoxide, tetrahydrofuran, triacetin and ethyl benzoate have also been evaluated for their impact on the initial drug burst. The biocompatibility and systemic toxicity of these organic solvents have been a major concern. In situ depot forming systems of PLGA have also been developed by Alza with the use of more lipophilic solvents such as benzyl benzoate (Alzamer®), which are claimed to be less irritating and which reduce the initial drug burst.

The SABER® system (Durect) consists of sucrose acetate isobutyrate (SAIB) dissolved in ethanol, benzyl alcohol, or other water miscible solvents. Owing to the low solution viscosity, the ease of administration with small gauge needles is an obvious advantage over the PLGA systems. A long-acting formulation of SABER-bupivacaine has been in clinical trials for post surgical pain management. The potential application of the SABER system for delivery of peptides and proteins has also been demonstrated by the seven day sustained release of recombinant human growth hormone ("rh-GH") in rats from a SABER suspension containing insoluble rh-GH powder and PLGA dissolved in the liquid phase. Thermosensitive biodegradable triblock copolymers have been developed by MacroMed as sustained release systems for parenteral drug delivery. The copolymer is comprised of hydrophobic PLGA blocks (A) and hydrophilic PEG blocks (B) with two distinct block configurations: ABA and BAB. ReGel® is an ABA-type triblock copolymer which is soluble in water. An aqueous solution of ReGel® is a free flowing liquid at 15° C., which transforms into a gel at body temperature when injected. The drug release rate is adjusted by changing the hydrophobic/hydrophilic content, polymer concentration, molecular weight and/or polydispersity of the triblock copolymer. Drugs can be dissolved, suspended or emulsified in ReGel®. OncoGel® is a product containing paclitaxel incorporated into ReGel® for local treatment of solid tumors. Paclitaxel is solubilized and entrapped within the hydrophobic domain of the gel and its release is sustained for six weeks as the gel undergoes degradation/erosion. The perivascular sustained delivery of paclitaxel in ReGel has also shown to effectively inhibit neointimal hyperplasia in vascular grafts in dogs. Because of the aqueous nature of ReGel®, prolonged sustained release (e.g. greater than 1 month) for a water-soluble drug may be difficult to achieve. Further high initial bursts of the drug cannot be avoided.

Poloxamer® 407 is an ABA triblock copolymer that consists of poly(oxyethylene) and poly(oxypropylene) units. It is a water-soluble non-ionic surfactant which forms an aqueous solution with reverse-thermal gelation properties. A solution with more than 20% of the polymer exhibits a low viscosity at low temperatures but rapidly forms a rigid semisolid gel network at body temperature. However, the parenteral application of Poloxamer® has been limited by its lack of biodegradability and concerns of cytotoxicity at high polymer concentration. Increase in plasma cholesterol and triglycerol levels in rats after intraperitoneal injection of the polymer can be also problematic.

The preparation of a poly(ethylene glycol)-based copolymer containing multiple thiol (—SH) groups along the polymer backbone has also been reported. When an aqueous solution of this copolymer was mixed with a cross-linking agent, $\alpha,\omega$-divinylsulfone-poly(ethylene glycol) (MW 2 KD) dissolved in a neutral phosphate buffer, a hydrogel was formed. A water-soluble drug can be dissolved in either solution and the drug becomes physically entrapped when the hydrogel is formed. Preliminary biocompatibility evaluation in rats and rabbits indicated mild adverse tissue reactions to the in situ cross-linked gels.

GelSite® (DelSite Biotech. Inc.) polymer is a natural acidic polysaccharide extracted and purified from the aloe plant. The polymer, in an aqueous solution, forms a gel in the presence of calcium when injected subcutaneously or intramuscularly; thus entrapping a water-soluble drug (i.e. a protein) in the solution and providing for sustained release. This binding provides additional control on the drug release without interfering with the biological functions of the proteins.

These systems are based on hydrophilic solutions of the polymer carrier in either water, NMP, polyethylene glycol and/or other diols in which upon immersion in water, the hydrophilic solvent is leached out to the surrounding tissue while the polymer precipitates. The limitations of such systems include the large volumes of polymer carrier and the solvent required for injection; burst release of drugs incorporated in the polymer solution due to the fast leach out of the hydrophilic solvent; use of toxic organic solvents, such as N-methylpyrrolidone (NMP); and slow degradation times of the polymers, e.g. months to years.

The objective of drug therapy is to maximize the therapeutic effect of the drug while minimizing adverse effects. Systemic delivery of drugs to localized tumors has the disadvantage of providing relatively low concentrations of the drug at proliferating cell boundaries which may be located far from the abnormal capillary networks in the tumor. Polymer-based anticancer drug loaded implants provide an opportunity to deliver high, localized doses of drug for a prolonged period directly into a tumor or at the site of tumor resection. Thus, injectable in situ setting semi-solid drug depots are being developed as alternative delivery systems. These implant systems are made of biodegradable products, which can be injected via a syringe into the body and once injected, gel to form a semi-solid depot. Biodegradable polyanhydrides and polyesters are useful materials for controlled drug delivery.

Ricinoleic acid-containing polyesters and polyanhydrides for use as drug carriers have been described in U.S. Patent Application Publication Nos. 2004/0161464, and 2004/0161464 to Domb. However, these polymers were prepared from ricinoleic acid monomers which resulted in a low degree of polymerization, in the range of 30 monomer units, and required a large ricinoleic acid content to obtain a pasty polymer. Also, these previously described polymers did not gel when placed in an aqueous medium.

In spite of the previously described drug delivery systems, there is still a need for a reliable polymer composition that can be injected into the body where it forms an in situ implant for the controlled release of drugs or serves as a temporary surgical implant.

It is therefore an object of the invention to provide biodegradable polyesters and polyester-anhydrides that are liquids or pastes at temperatures below 37° C., that gel upon immersion in aqueous media or tissue and methods of making and using thereof. It is further the object of the invention to convert commonly used solid homo and copolyesters of polyhydroxy alkanoic esters made from lactic, glycolic and hydroxyl caproic acid into a liquid or paste by incorporation of a relatively small amount of ricinoleic acid oligomers.

It is further the object of this invention to convert commonly used solid homo and copolyanhydrides of alkane dicarboxylic acids into a liquid or paste by incorporation of ricinoleic acid oligomers into the polymer backbone.

It is further the objective of this invention to provide sustained release of a pharmaceutically active agent for at least one week, preferably for at least four weeks biodegradable polyesters and/or polyanhydrides, which are liquids or pastes below 37° C.

It is further an object of the invention to provide biodegradable polyesters and polyester-anhydrides that are liquids or pastes at temperatures below 37° C., that gel upon immersion in aqueous media or tissue that degrade completely in about 12 weeks.

It is further the object of this invention to provide pasty biodegradable compositions that can serve as sealants and temporary shields for adhesion prevention of internal organs.

It is further the object of this invention to provide low cost pure ricinoleic acid from crude ricinoleic acid or castor oil.

SUMMARY OF THE INVENTION

Biodegradable carriers synthesized from ricinoleic acid oligoesters and aliphatic molecules having at least one carboxylic acid and at least one hydroxy or carboxylic acid group that are liquids or pastes at temperatures below 37° C. and methods of making and using thereof are described herein. The polymers described herein significantly increase their viscosity upon immersion in aqueous medium. These polymers can be used as hydrophobic biomedical sealants, temporary barriers to prevent adhesions, cell supports, carriers for drug delivery, and coatings on implantable medical devices, such as stents. The polymers made from ricinoleic acid oligoesters are less viscous and easier to inject compared to polymers of similar composition and molecular weight prepared from ricinoleic acid monomers, possess a higher molecular weight, retain an incorporated drug for longer periods, and degrade into soft degradation products at a slower rate compared with polymers synthesized from ricinoleic acid monomers. Pharmaceutically active agents can be incorporated into the liquid or pastes without the use of organic solvents.

Immersion of the compositions in aqueous medium, such as body fluids, increases the viscosity of the composition resulting in the formation of a semisolid material. In one embodiment, the polymeric material is a polyester, or a poly(ester-anhydride), composed of ricinoleic acid oligomer and aliphatic molecules having at least one carboxylic acid and at least either an hydroxyl or carboxylic acid groups.

BRIEF DESCRIPTIONS OF THE DRAWINGS

The file of this patent contains at least one drawing executed in color photograph. Copies of this patent with color photograph(s) will be provided by the Patent and Trademark Office upon request and payment of necessary fee.

Figure 4:
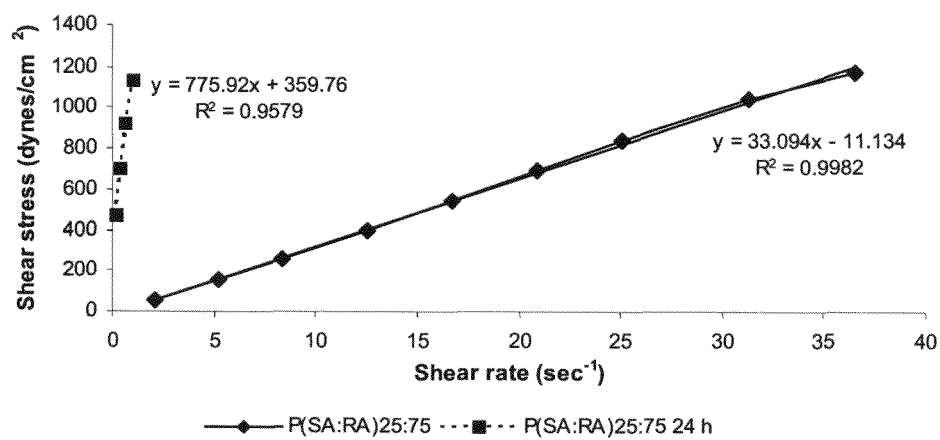

FIG. 4 is a graph showing the relationship between shear rate ($sec^{-1}$) and shear stress ($dynes/cm^2$) before and after exposure of p(SA:RA) (3:4) to a phosphate buffer. Measurements were performed at 23° C. The solid line shows the polymers before exposure to the phosphate buffer and the dashed line shows the polymer after exposure to the phosphate buffer.

Figure 5:
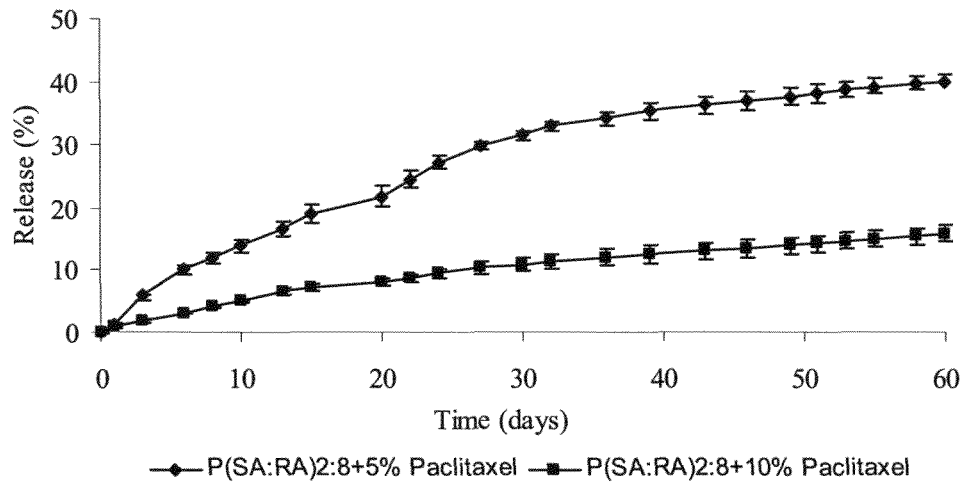

FIG. 5 shows the in vitro cumulative release of paclitaxel from P(SA:RA) (2:8) loaded with 5% w/w and 10% w/w paclitaxel. Each point represents the mean value±STD(n=3). Release was conducted in 0.1M phosphate buffer, pH 7.4, at 37° C. Paclitaxel concentrations were determined by HPLC.

Figure 6A:
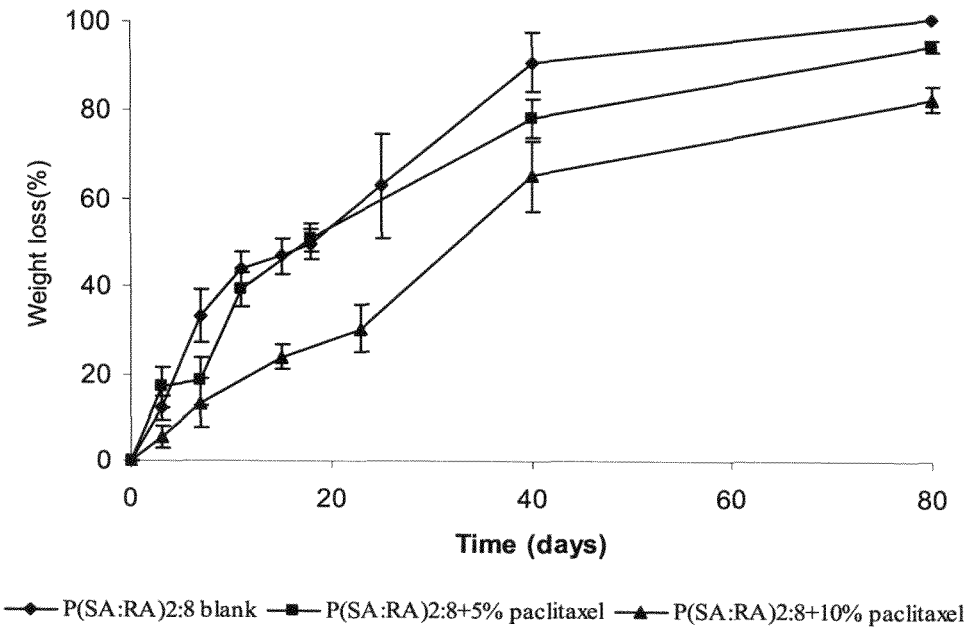
Figure 6B:
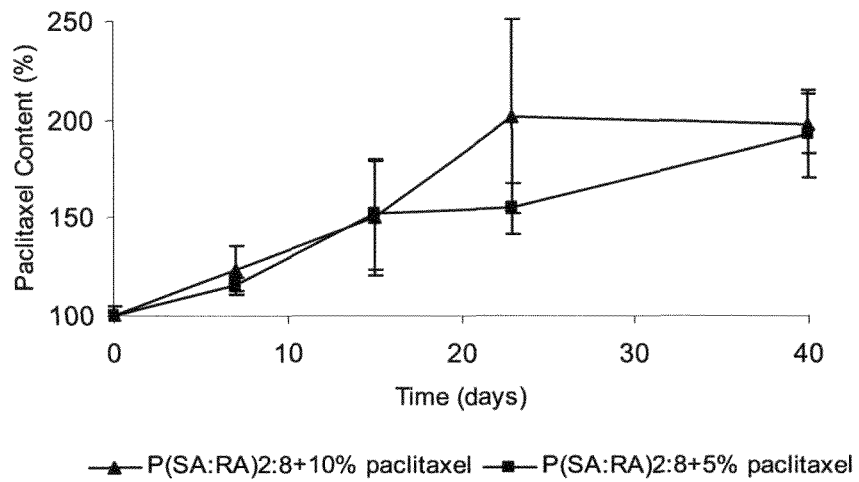

FIG. 6 shows the in vitro hydrolytic degradation and loaded and unloaded P(SA:RA) (2:8). FIG. 6a shows the in vitro hydrolytic degradation of P(SA:RA) (2:8) blank and loaded with 5% w/w and 10% w/w paclitaxel monitored by weight loss of the degrading sample. FIG. 6b shows paclitaxel accumulation in the sample during in vitro hydrolytic degradation (determined by NP HPLC). The in vitro hydrolytic degradation was conducted in phosphate buffer solution (50 ml, 0.1 M, pH 7.4) at 37° C. with constant shaking (100 RPM).

Figure 7:
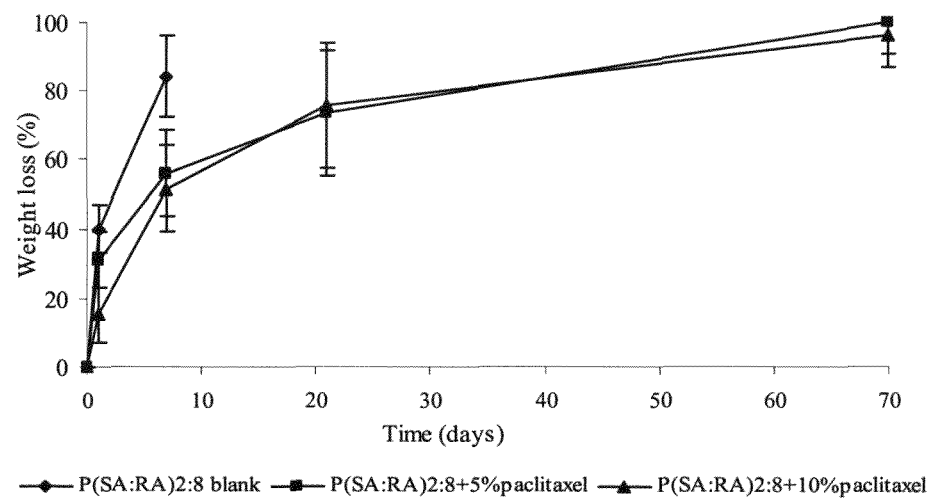

FIG. 7 shows the in vivo degradation of blank polymer and paclitaxel formulations (5% and 10%) injected subcutaneously in C3H healthy mice. At each time point (days 1, 7, 21 and 70), the mice (n=4) were sacrificed and the polymer implant was examined for Mw, weight and paclitaxel content.

Figure 8:
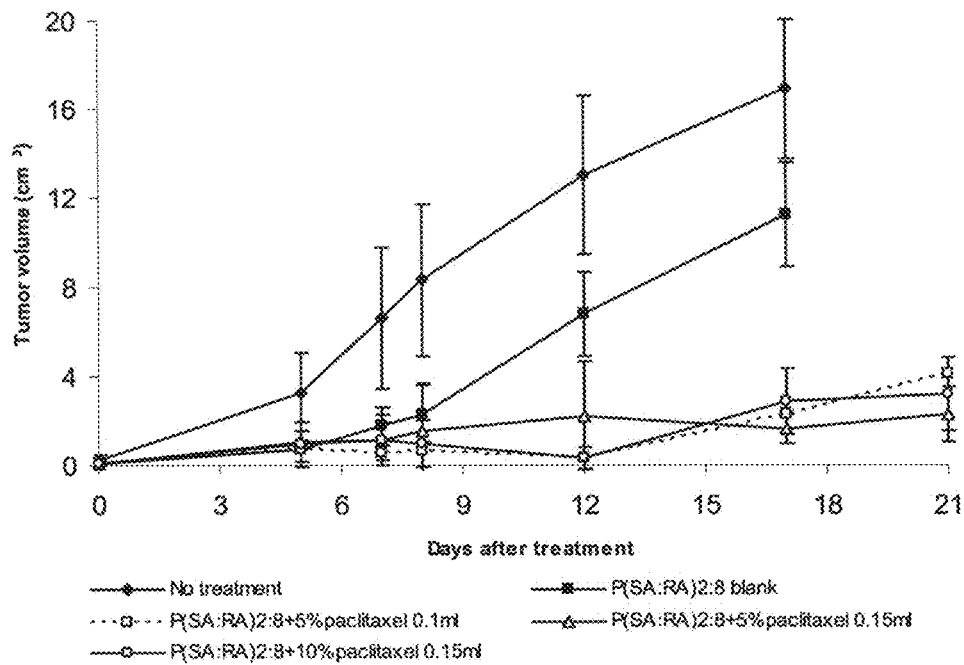

FIG. 8 shows the in vivo anti-tumor effect of paclitaxel formulations against MBT heterotrophic model in C3H mice.

Treatment started eight days after tumor cells inoculation. Time zero represents the initiation of the treatment. Each point represents mean±STD (n=10).

Figure 9:
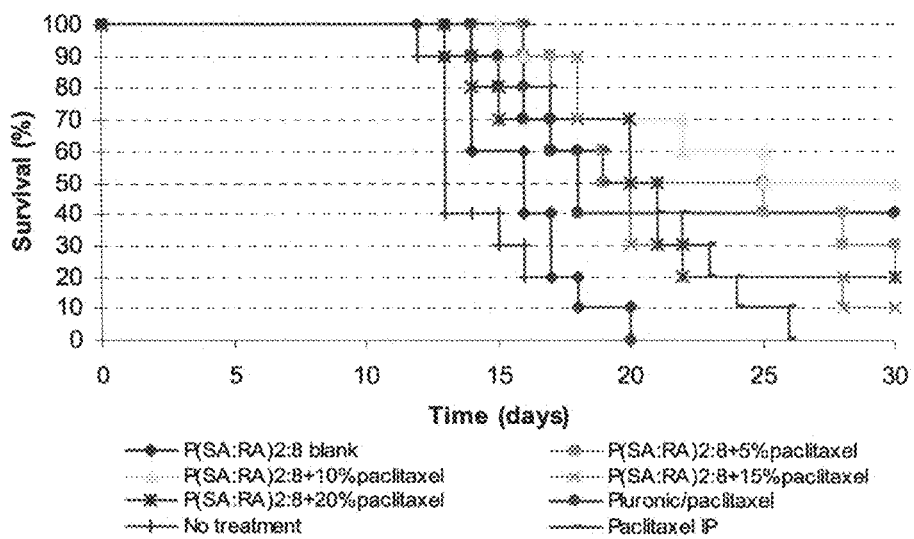

FIG. 9 shows the evolution of survival following the inoculation of C57B1/6 rats with B16F1 and treated with P(SA:RA) (2:8) loaded with different concentrations of paclitaxel.

Figure 10:
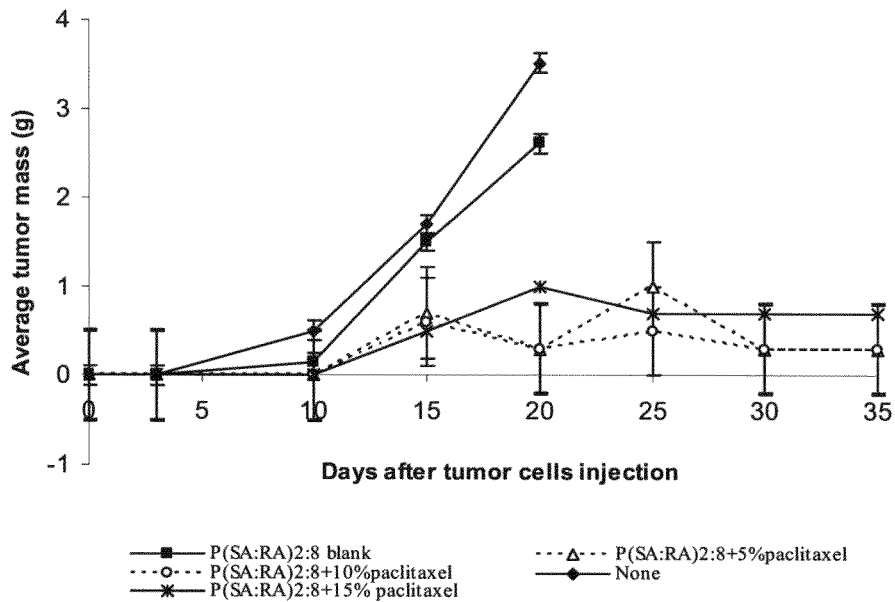

FIG. 10 shows the evolution of tumor mass following the inoculation of C57B1/6 rats with B16F1 and treated with P(SA:RA) (2:8) loaded with different concentrations of paclitaxel.

Figure 11:
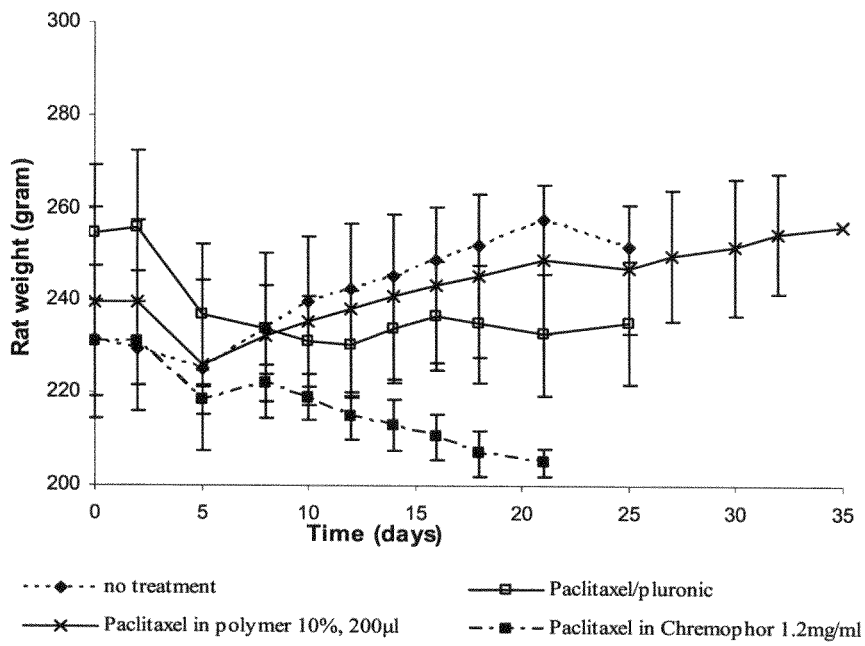

FIG. 11 shows the evolution of the average weight of the rats in all treatment groups during the experiment. Standard deviation is shown by the error bars.

Figure 12:
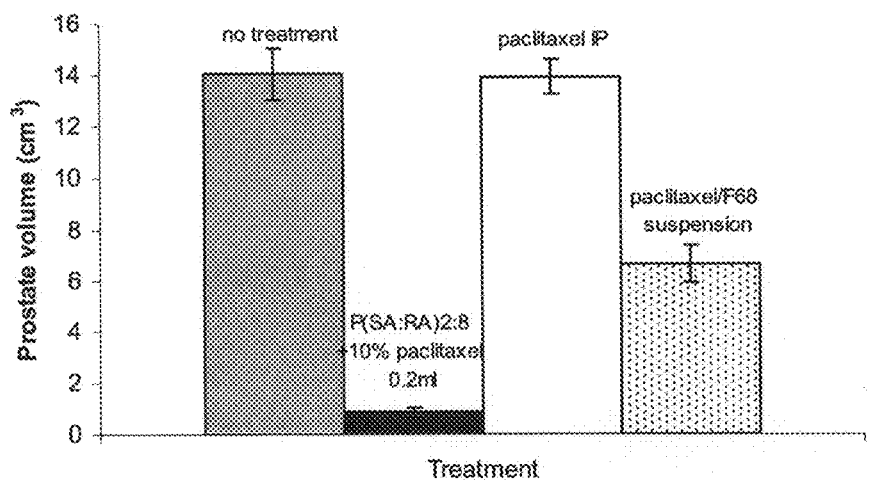

FIG. 12 shows the evolution of the tumor volume at death for different treatment groups.

Figure 13:
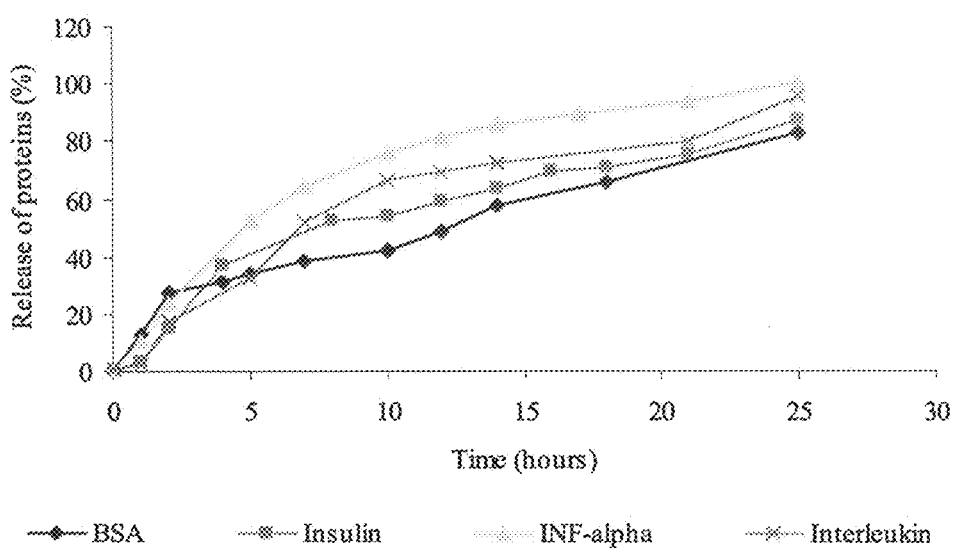

FIG. 13 shows the percent in vitro release of bovine serum albumin ("BSA"), insulin, interferon-alpha ("INF-alpha") and interleukin from p(SA:RA) (20:80) and p(SA:RA) (30:70) w/w as a function of time (hours). The release of peptides was conducted in 0.1 M phosphate buffer (pH 7.4) at 37° C. The drug content in the releasing medium was determined by the Lowry protein assay.

Figure 14:
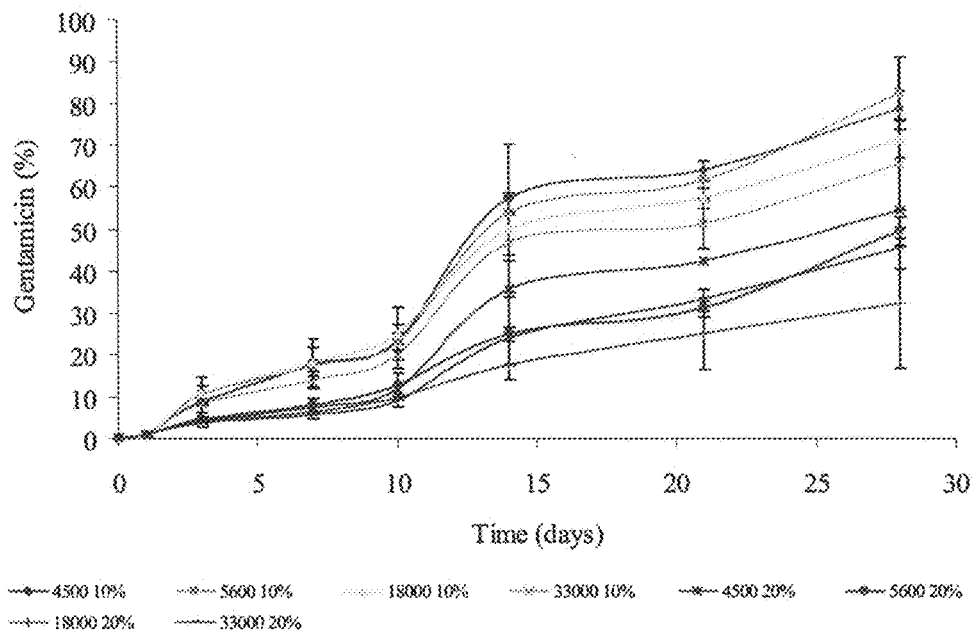

FIG. 14 shows the percent in vitro release of gentamicin from p(SA:RA) (3:7) of different molecular weights as a function of time (days).

Figure 15:
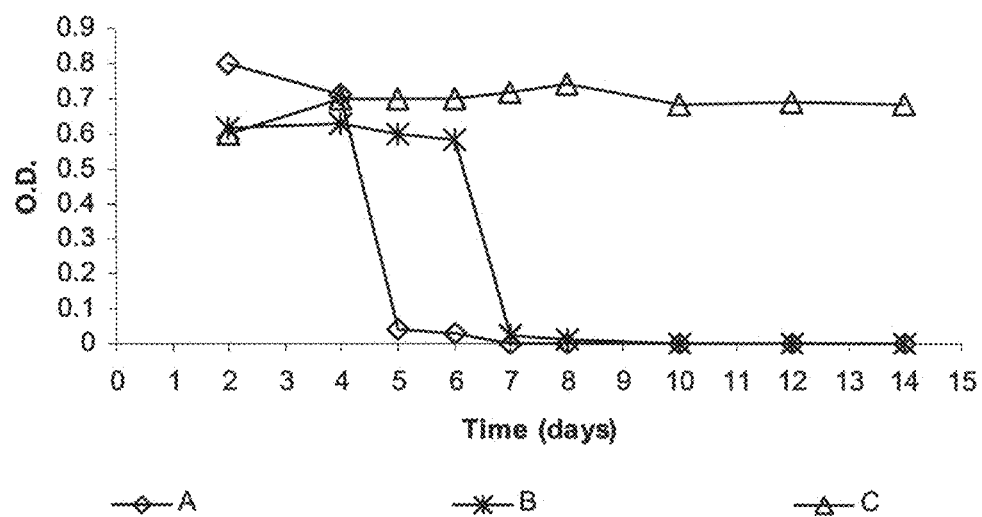

FIG. 15 is a graph showing bacterial concentration (optical density) versus time (days) for three different dilutions.

Figure 16A:
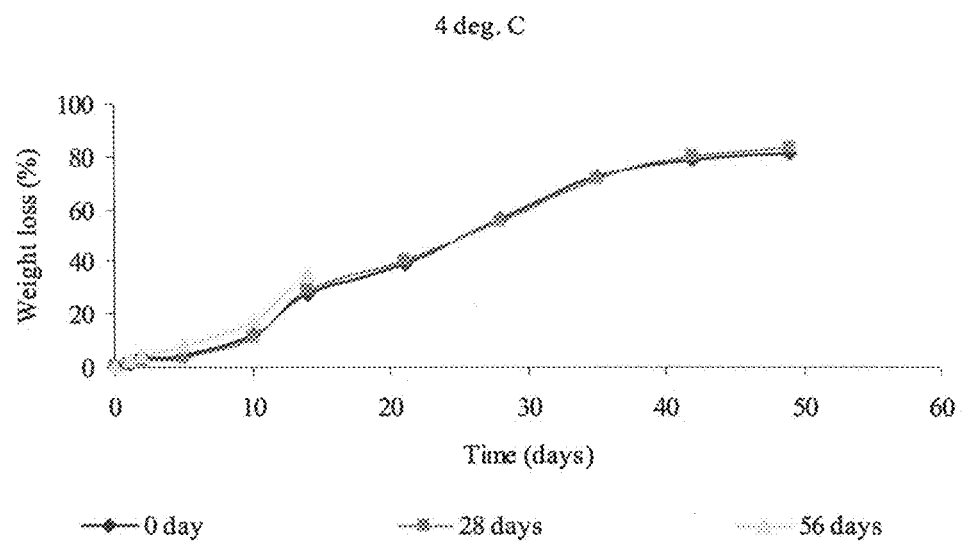
Figure 16B:
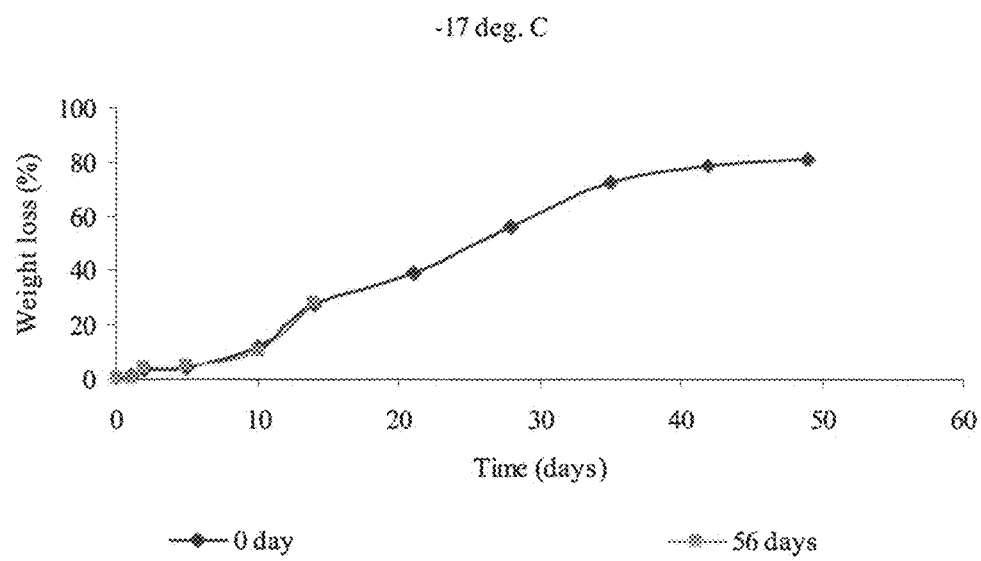

FIG. 16 shows the release of gentamicin after storage at 4° C. and −17° C. for eight weeks as a function of time (days). FIG. 16a shows the release of gentamicin from a formulation stored at 4° C. for 8 weeks. FIG. 16b shows the release of gentamicin from a formulation stored at −17° C. for 8 weeks.

DETAILED DESCRIPTION OF THE INVENTION

I. Compositions

A. Polymers

Biodegradable carriers synthesized from ricinoleic acid oligoesters and aliphatic molecules having at least one carboxylic acid and at least one hydroxy or carboxylic acid group that are liquids or pastes at temperatures below 37° C. and that significantly increase their viscosity upon immersion in aqueous medium are described herein. The polymers have a molecular weight of at least 3,000 Daltons, preferably at least 7,000 Dalton, more preferably at least 10,000 Daltons. The polymer can have varying degrees of polymerization. In one embodiment, the polymer has a degree of polymerization of at least 40.

Ricinoleic acid (cis-12-hydroxyoctadeca-9-enoic acid) is a $C_{18}$ fatty acid with a cis-configured double bond in the $9^{th}$ position and a hydroxyl group in the $12^{th}$ position. Crude ricinoleic acid can be purchased commercially or prepared by the hydrolysis of castor oil. Castor oil is a natural triglyceride that contains on average about 3 hydroxyl groups per molecule. Castor oil is extracted from castor beans, typically by pressing, and is approximately 90% ricinoleate (12-hydroxyoleate).

Ricinoleic acid can be reacted with one or more polyanhydrides to produce ricinoleic acid oligoester prepolymers, which are further polymerized to produce the final polymer. Suitable polyanhydrides can be prepared by the polymerization of aliphatic and/or aromatic dicarboxylic acids. Suitable dicarboxylic acids include, but are not limited to, malonic, succinic, glutaric, adipic, sebacic, pimelic, suberic and azelaic acid. Suitable unsaturated diacids include fumaric acid, itaconic acid, and maleic acid. Long chain diacids having more than 10, more than 15, more than 20, and more than 25 carbon atoms such as dimer oleic acid and dimer erucic acid and polycarboxylic acids such as trimer erucic or trimer oleic acids, polyacrylic acid derivatives and citric acid can also be used. The dicarboxylic acids may also contain reactive functional groups, such as amino and/or hydroxyl groups.

Ricinoleic acid can also be copolymerized with a hydroxyalkanoic acid to produce polyesters containing ricinolate monomer units. Suitable hydroxyalkanoic acids include, but are not limited to, lactic acid; glycolic acid; hydroxycaproic acid; 3, 4, and 5 hydroxyalkanoic acids and mixtures thereof.

The polymers described herein are biodegradable and biocompatible. In one embodiment, the polymers complete degrade in about 12 weeks.

B. Active Agents

The polymer compositions described herein can be used to deliver therapeutic, diagnostic, and/or prophylactic agents.

Exemplary drug agents useful for forming the composition described herein include, but are not limited to, analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; anihelminthic agents; antihistamines; antihyperlipidemic agents; antihypertensive agents; anti-infective agents; anti-inflammatory agents; antimigraine agents; antineoplastic agents; antiparkinsonism drugs; antipruritic agents; antipsychotic agents; antipyretic agents; antispasmodic agents; antitubercular agents; antiulcer agents; antiviral agents; anxiolytic agents; appetite suppressants (anorexic agents); attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; sialagogues, steroids; smoking cessation agents; sympathomimetics; tranquilizers; vasodilators; beta-agonist; tocolytic agents, and mixtures thereof. In one embodiment, the active agent is an anticancer agent, such as paclitaxel or methotrexate. In another embodiment, the active agent is an antibiotic, such as gentamicin. In still another embodiment, the active agent is a peptide or protein.

An effective amount of these agents can be determined by one of ordinary skill in the art. Factors to consider in determining a therapeutically effective amount include age, weight and physical condition of the person to be treated; type of agent used, type of polymer used; and desired release rate. Typically, the concentration of the active agent is from about 1% to about 90% by weight of the compositions, preferably from 5% to about 60% by weight of the composition, more preferably from about 5% to about 20% by weight of the composition.

C. Carriers, Additives, and Excipients

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes, but is not limited, to surfactants, diluents, buffers, salts, and preservatives or stabilizers. Stabilizers are used to inhibit or retard drug decomposition reactions which include, by way of example, oxidative reactions.

II. Methods of Making

The polymers described herein can be prepared by a variety of methods known in the art. Poly(ricinoleic acid-anhydride) copolymers can be prepared by melt condensation. In one embodiment, an aliphatic or aromatic dicarboxylic acid is reacted with acetic anhydride to form a polyanhydride prepolymer. The prepolymer is heated under high vacuum to form a polyanhydride. Low molecular weight poly(ricinoleic acid-anhydride) copolymers can be prepared by the esterification of a polyanhydride with ricinoleic acid.

Alternatively, higher molecular weight poly(ricinoleic acid-anhydride) copolymers can be prepared by the esterification of a polyanhydride with oligomers of ricinoleic acid at ambient pressure under an inert atmosphere. The reaction is terminated when the molecular weight of the polymer is 1000 Daltons. Acetic anhydride is added to the polymer and the solution is heated for 30 minutes. The excess acetic anhydride is removed resulting in an oily prepolymer. The prepolymer is polymerized with heat under high vacuum to form the final polymer. The molecular weight of the final polymer is dependent on the reaction time as well as the purity of the ricinoleic acid. For example, polymers prepared with pure ricinoleic acid monomer had a maximum molecular weight of 8,000. In contrast, polymers prepared from crude ricinoleic acid (85% ricinoleic acid content) had a maximum molecular weight of 3,500 Daltons.

Polyesters containing ricinoleic acid monomer units can be prepared by reacting a hydroxyalkanoic acid, such as L-lactic acid, D,L-lactic acid, glycolic acid, hydroxycaproic acid, and mixtures thereof with castor oil in the presence of $H_3PO_4$ as a catalyst.

The polymers can be loaded with one or more therapeutic, diagnostic, and/or prophylactic agents by direct mixing of the polymer and agent without the need for heat and/or solvents. The polymer and drug are mixed until a smooth paste is formed. One or more additives can be added to the drug-loaded polymers to reduce the viscosity and/or improve the injectability of the formulations. Examples of suitable additives include, but are not limited to, ricinoleic acid, phospholipids, PEG 400, and PEG 2000. If additives are used, typically, the drug is first mixed with the additive(s) and then the drug-additive(s) mixture is incorporated into the polymer. Again, the additives can be mixed with the drug and polymers directly, without the need for heat and/or solvents.

III. Methods of Use

The polymeric compositions described herein can be used as degradable carriers for treating local diseases such as cancer, bacterial and fungi local infections and pain. Site-specific chemotherapy that provides high drug concentrations for an extended time period in the diseased site is an effective way of treating remnant infected cells after resection of the infected area such as solid tumors. Typically the formulation is administered by injection and/or implantation, intramuscularly, subcutaneously, intraperitoneally, and/or intratumor (before, during or after tumor resection). The polymers are liquid or pastes at room temperatures such that they can be injected or implanted without the need for additives. However, additives can be added to reduce the viscosity and/or improve the injectability of the compositions as needed.

Of specific interest is the application of these polymers for site-specific chemotherapy for the treatment of solid tumors including: squamous cell carcinoma (SCC) of the head & neck, prostate cancer, and sarcomas for intratumoral injection or insertion. Cancer of the head and neck accounts for about 40,000 new cases every year in the United States, which is about 5% of all new cancer cases in the United States. Unlike other solid tumors, the most common manifestation of recurrence of head and neck cancer is regional, that is, recurrence in the neck. A prospective device based on the polymers of this invention is a pasty or liquid polymeric implant, made of a biodegradable polymer matrix loaded with an anticancer agent. The anticancer agent, such as Methotrexate or Paclitaxel, is homogeneously dispersed into the polymer matrix. The active drug is released in a controlled manner to the surrounding tissue, when placed in contact with body fluids, while the polymer carrier is eliminating by slow degradation.

The implant, in a form of an injectable liquid or paste, is injected into the tumor or inserted into the tumor site during the surgical procedure of tumor removal. The implant provides a high dose of anti-cancer drug for an extended period of time, typically days, weeks or months, in the tumor site, with minimal systemic drug distribution, thus, providing a localized treatment of the residual tumor cells as a complementary drug therapy to the surgery.

The same concept of long term drug delivery to specific diseased body sites applies also to other solid tumors, local infections such as osteomyelitis-bone infection, local anesthetic delivery for cancer or AIDS patients and drugs that control tissue growth such as heparin and steroids for treating restenosis and keloids.

The polymers can also be used as coatings on implantable medical devices, such as stents, as surgical sealants or as barriers for the reduction of organ to organ adhesion.

EXAMPLES

Materials and Instrumentation

Ricinoleic acid (RA) 85% pure was obtained from Fluka, Buch, Switzerland and purified to 97% determined by chromatography. Sebacic acid (SA) 99%, Adipic acid, fumaric acid, maleic anhydride, and succinic anhydride were obtained from Sigma-Aldrich (Israel). All solvents were analytical grade from BioLab (Jerusalem, Israel) or Frutarom (Haifa, Israel) and were used without further purification.

Molecular weights of the poly(ester-anhydrides) were estimated on a gel-permeation chromatography (GPC) system consisting of a Waters 1515 isocratic HPLC pump with Waters 2410 refractive index (RI) detector, a Rheodyne (Coatati, Calif.) injection valve with 20-µL loop (Waters Ma). Samples were eluted with chloroform through a linear column at a flow rate of 1 mL/min. The molecular weights were determined relative to polystyrene standards (Polyscience, Warrington, Pa.).

Infrared (IR) spectroscopy (Perkin Elmer, 2000 FTIR) was performed on prepolymers, polymer samples and on hydrolyzed samples cast onto NaCl plates from dichloromethane solution.

Thermal analysis was determined on a Mettler TA 4000-DSC differential scanning calorimeter, calibrated with zinc ("Zn") and indium ("In") standards, at a heating rate of 10° C./min (average sample weight 10 mg) and on a Stuart Scientific SMP1 melting-point heater.

Cryo-scanning electron microscopy (Cryo-SEM) was conducted using Quanta 2000 SEM (30 kV).

Light Microscopy was conducted by microscopic observations of the samples under stereomicroscope Stemi SV11 (Zeiss, Germany) equipped with Digital camera Cooplix 990 (Nikon, Japan).

Viscosity of the polymers was determined using the rotational method (Brookfield programmable rheometer, LV-DV-III). Cylindrical spindle LV4 was used.

Example 1

Preparation of Poly(Ricinoleic Acid-Sebacic Acid) Copolymers

Preparation of Pure Ricinoleic Acid

Castor oil was dissolved in 2 volumes of 2 N KOH in ethanol at room temperature for a few hours with continuous stirring. The resulting potassium ricinoleate precipitate in ethanol was mixed with isopropyl ether to better separate the precipitate, and the mixture was allowed to separate. The precipitate slurry was centrifuged to separate the solids and the solvent was decanted. The ricinoleic acid potassium salt was dispersed in iced 1N HCl solution and extracted with ethyl acetate. After solvent evaporation, a slightly yellow oil was obtained which contained 100% fatty acids of which at least 95% was ricinoleic acid as determined by gas chromatography.

Polymer Synthesis

PSA (poly(sebacic acid)) was prepared by melt condensation. Sebacic acid was boiled in acetic anhydride for 20 minutes. The acetic anhydride was evaporated to dryness to obtain an off white prepolymer of sebacic acid. To prepare PSA, the sebacic acid prepolymer was heated to 140° C. under high vacuum ($1.3 \times 10^{-1}$ mbar) for 3 hours to obtain the poly(sebacic acid) having a Mw>30000 Da. Low molecular weight (AS3-102, AS3-101, AS3-92) poly(sebacic acid-co-ricinoleic acid) (p(SA:RA)) copolymers were prepared by esterification of PSA with ricinoleic acid (RA, Mw 298 Da). Higher molecular weight (p(SA:RA)) copolymers were prepared (AS3-114, AS3-104) by esterification of PSA with oligomers of RA (Mw~2100-3500 Da). Transesterification is done in 3:7 w/w ratio for P(SA:RA) (3:7) (AS3-101, AS3-102, AS3-114) and in 2:8 ratio for P(SA:RA) (2:8) (AS3-92, AS3-104). The reaction was done in a dry flask in bulk under a nitrogen atmosphere at 120° C. for 3-4 hours. The reaction was terminated when a molecular weight of 1000 Daltons was achieved. After that, acetic anhydride was added (1/1 w/w). The solution was refluxed for 30 min at 140° C. and the excess acetic anhydride and acetic acid was evaporated to dryness to produce a viscous yellow oil. The oily prepolymer was polymerized at 140° C. under a vacuum of 0.19-0.32 mm Hg for 4 to 8 hours, depending on the desired molecular weight. For the polymers prepared from ricinoleic acid oligomers, the longer the reaction time the higher the resulting molecular weight of the polymer. For the polymers prepared with ricinoleic acid monomer, the highest MW reached was Mw=8,000. For the polymers prepared from crude ricinoleic acid, 85% ricinoleic acid content, a molecular weight of up to 3,500 was obtained.

Results and Discussion

The tables below provide the molecular weight of the polymers. The polymers were prepared as described above.

TABLE 1

Weight average and number average molecular weights of P(SA:RA)3:7

| Name | Component A | Component B | Mw, Mn |
|---|---|---|---|
| 1 | PSA | Ricinoleic acid (RA) 95% pure | Mw 6400 Mn 4000 |
| 2 | PSA | Ricinoleic acid 85% pure | Mw 3400 Mn 2300 |
| 3 | PSA | Ricinoleic acid 99% pure | Mw 7000 Mn 5000 |
| 4 | PSA | RA oligomer (Mw 2100) RA oligomer (Mw 600) | Mw 68600 Mn 49000 |
| 5 | PSA | | Mw 18000 Mn 12000 |

PSA—poly(sebacic anhydride), Mw = 38,000; Mn = 22,000 prepared by melt condensation of sebacic acid using acetic anhydride as dehydrating agent.

TABLE 2

Weight average and number average molecular weights of P(SA:RA)2:8

| Name | Component A | Component B | Mw, Mn (Da) |
|---|---|---|---|
| 6 | PSA | RA 95% pure | Mw 3700 Mn 3200 |
| 7 | PSA | RA 85% pure | Mw 2100 Mn 1400 |
| 8 | PSA | RA oligomer (Mw 3500) | Mw 18200 Mn 13400 |
| 9 | PSA | RA oligomer (Mw 1200) | Mw 16500 Mn 11300 |

PSA—poly(sebacic anhydride), Mw = 38,000; Mn = 22,000 prepared by melt condensation of sebacic acid using acetic anhydride as dehydrating agent.

TABLE 3

Polymers prepared from other diacids

| Name | Component A | Component B | Molecular status at 37° C. |
|---|---|---|---|
| 10 | PAA | Ricinoleic acid (RA) 95% pure | Mw 3400 IL Mn 2300 |
| 11 | PAzA | Ricinoleic acid 95% pure | Mw 5000 IP Mn 3200 |
| 12 | PFA | Ricinoleic acid 95% pure | Mw 3000 IP Mn 2000 |
| 13 | PAzA | RA oligomer (Mw 2100) RA oligomer (Mw 2100) | Mw 42000 IP Mn 28000 |
| 14 | PSubA | | Mw 35000 IP Mn 17000 |

PAA—poly(adipic anhydride), Mn = 38,000; PFA—poly(fumaric anhydride), Mn = 14,000; PAzA—poly(azelaic anhydride), Mn = 32,000; PSubA—poly(suberic anhydride) Mn = 27,000, IL—injectable liquid; IP—injectable paste.

Example 2

Liquid Poly(Ester-Anhydride)s-Based on Ricinoleic Acid and Various Fatty Diacids Synthesis Poly(Fumaric-co-Ricinoleic-Ester-Anhydride) 3:7 w/w Ratio 20 grams of fumaric acid (FA) were refluxed in acetic anhydride for 2 hours. The acetic anhydride was evaporated and the residue was polymerized at 170° C. for 4 hours to obtain poly(fumaric acid) (PFA) having a molecular weight of 20,000. 50 grams of ricinoleic acid (RA) oligomers (Mw=700) were added and after 4 hours of transesterification at 120° C., the molecular weight of the polymer dropped to 1200 Daltons. The oligomers were activated by acetic anhydride and repolymerized. The resulting polymer had a Mw of 15000 and a Mn of 8000. DSC MP peak at 34° C. IR: 1732 cm$^{-1}$ and 1819 cm$^{-1}$ Poly(Adipic-co-Ricinoleic-Ester-Anhydride) 2.8 w/w Ratio 20 grams of adipic acid (AA) were refluxed in acetic anhydride for 30 minutes. The acetic anhydride was evaporated and the adipic acid prepolymer was polymerized at 170° C. for 4 hours to produce a polymer having a molecular weight of 27000 Daltons. 50 grams of RA were added and after 4 hours of transesterification at 120° C., the molecular weight of the polymer dropped to 900. The oligomers were activated by acetic anhydride and repolymerized. The resulting polymer had a Mn of 4000 and a Mw of 6000. The melting point of the polymer was 10° C. IR: 1732 cm$^{-1}$ and 1819 cm$^{-1}$. NMR: 5.3 ppm and 5.4 ppm (CH=CH), 4.8 ppm (CH—O—CO), 1.6 ppm (CH$_2$—CH$_2$—CH$_2$ adipic acid). Similarly, polymers were prepared from ricinoleic acid oligomers of Mw=2200 to yield a liquid polymer of Mw=15,000.

Poly(Succinic-co-Ricinoleic-Ester-Anhydride) 1:1 m/m Ratio 36 grams (0.12 mol) of RA and succinic anhydride (24 grams, 0.24 mol) were refluxed in toluene overnight. The solvent was evaporated and the product was dissolved in dichloromethane, filtered and washed 4 times with doubly distilled water (DDW) to dissolve the unreacted succinic anhydride. The yield was 67%. NMR confirmed the ester formation—4.8 ppm (CH—O—CO). The product was refluxed in acetic anhydride (1:10 w/v) for 30 minutes and evaporated till dryness. The prepolymer was polymerized by anhydride condensation. After 4 hours, the Mn=4200 and the Mw=6200. The meting point of the polymer was -2° C. IR: 1732 cm$^{-1}$ and 1819 cm$^{-1}$. NMR: 5.3 ppm and 5.4 ppm (CH=CH), 4.8 ppm (CH—O—CO), 2.6 ppm (CO—CH$_2$—CH$_2$—CO succinate). polymers were prepared from ricinoleic acid oligomers of Mw=2200 to yield a liquid polymer of Mw=20,000.

Poly(maleic-co-Ricinoleic-Ester-Anhydride) 1:1 m/m Ratio 36 grams (0.12 mol) of RA and maleic anhydride (24 grams, 0.24 mol) were refluxed in toluene overnight. The solvent was evaporated and the product was dissolved in dichloromethane, filtered and washed 4 times with DDW to dissolve the unreacted maleic anhydride. The yield was 72%. NMR confirmed the ester formation—4.8 ppm (CH—O—CO). The product was refluxed in acetic anhydride (1:10 w/v) for 30 minutes and evaporated till dryness. The prepolymer was polymerized by anhydride condensation. After 4 hours, the Mn=4700 and the Mw=7000. The melting point of the polymer was -8° C. After 24 hours, the Mn=11000 and the Mw=14000 (constant). IR: 1732 cm$^{-1}$ and 1819 cm$^{-1}$. NMR: 5.3 ppm and 5.4 ppm (CH=CH), 4.8 ppm (CH—O—CO), 6.8 ppm and 6.2 ppm (CO—CH$_2$=CH$_2$—CO maleate). Similarly, polymers were prepared from ricinoleic acid oligomers of Mw=2200 to yield a liquid polymer of Mw greater than 15,000.

Poly(succinic-co-Oligoricinoleic-Ester-Anhydride) 1:1 m/m Ratio

Oligomers of RA were prepared by esterification of RA in bulk at 120° C. for 7 hours. The obtained molecular weights were: 300, 900, 1200, and 2100 (1, 3, 4, and 7 repeating units), average molecular weight was Mn~950.

40 grams (0.04 mol) of RA oligomer and succinic anhydride (8.4 grams, 0.08 mol) were refluxed in toluene overnight. The solvent was evaporated and the product was dissolved in dichloromethane, filtered and washed 4 times with DDW to dissolve the unreacted succinic anhydride. The product was refluxed in acetic anhydride (1:10 w/v) for 30 minutes and evaporated till dryness. The prepolymer was polymerized by anhydride condensation to yield high molecular weight polymers. IR: 1732 cm$^{-1}$ and 1819 cm$^{-1}$. NMR: 5.3 ppm and 5.4 ppm (CH=CH), 4.8 ppm (CH—O—CO), 2.6 (CO—CH$_2$—CH$_2$—CO succinate). Similar polymers were prepared from maleic anhydride by replacing succinic anhydride with maleic anhydride. NMR: 5.3 ppm and 5.4 ppm (CH=CH), 4.8 ppm (CH—O—CO ricinoleic acid ester), 4.9 ppm (CH—O—CO ricinololyl maleate ester), 6.8 ppm and 6.2 ppm (CO—CH$_2$=CH$_2$—CO maleate).

Example 3

Gelling Behavior and In Vivo Evaluation of Poly(Ester Anhydride) Polymers Prepared from Ricinoleic Acid The gelation behavior of the polymers was evaluated using thermal analysis, light microscopy, cryo-scanning electron microscopy, and viscosity measurements.

Light Microscopy

The differences between the polymer before and after exposure to buffer were examined by microscopic observations of the samples under stereomicroscope Stemi SV11 (Zeiss, Germany) equipped with a Digital camera (Cooplix 990, Nikon, Japan) for image recording. Image recording was performed in the normal quality mode applying different microscope zoom magnifications together with zoom of the digital camera adjusted to the best visual resolution. Illumination was performed by reflected light, supplied by KL 1500 Electronic illumination systems (Zeiss, Germany).

Upon contact of the polymers with an aqueous medium, changes in the polymer sample were visible. The polymer before exposure to buffer (dry polymer) was transparent while, after the gelation process took place (8 hours in buffer), the polymer was opaque. When the polymer was cut, two distinct regions were found: an outer region which was a gel (1) and the core (2) which appeared as a soft matrix.

Cryo-Scanning Electron Microscopy (Cryo-SEM)

Wet and dry polymer samples were fixed on a stub, frozen with liquid nitrogen under high vacuum, and then gold-coated using a Polarone E5100. To prepare the polymer samples for Cryo-SEM, the polymers were injected into a buffer solution (0.1 M, pH 7.4). After 24 hours the sample was pulled out and put on a stub without drying. The sample was frozen with liquid nitrogen under high vacuum. The frozen sample was gold-coated using Polarone E5100.

Removal of the absorbed water from the exposed polymer (by drying or lyophylisation) converted the polymer to an oil with the same characteristics as before the polymer was exposed to water. Cryo-microscopy allowed freezing the sample while it still contained the absorbed water and thus it was possible to visualize the polymer when it was affected by the aqueous medium. The polymer before exposure to buffer (dry polymer) had a homogenous surface, while the polymer sample exposed to water showed a defined structure at the outer layer that was close to the aqueous medium. The polymer chains, exposed to water, formed a kind of a rigid network across the drop of the polymer sample injected to the water. This network caused the polymer drop to keep its shape in the aqueous medium. A Cross-section of the polymer droplet showed that the inside of the polymer remained intact, similar to the polymer before exposure to the aqueous phase. These findings show that gelation of the polymer occurred only on the surface that was in contact with the aqueous medium.

Water Absorption

Polymer samples (P(SA:RA) (3:7) and P(SA:RA) (2:8) were put in a phosphate buffer (pH 7.4, 0.1 M, 37° C.) and the KF titration was performed after 0, 4, 12, 26, and 40 hours of exposure to the buffer. A separate polymer sample was prepared for each time point. At each time point, the polymer was taken out of the buffer, blotted on absorbent paper, weighed, and dissolved in 1 ml dichloromethane. The polymer solution was placed in the titration pot. Direct titration was performed in methanol using regular KF reagents. The sample from the inner core of the specimen was prepared similarly.

Differential Scanning Calorimetry

The endotherms of P(SA:RA) (3:7) at different durations of exposure to buffer were taken. Before exposure of the polymer to buffer there is one transition that peaks at 35° C. After 3 hours in buffer the peak was at 38.3° C., and at 12 hours in buffer the transition became 45° C. At 24 hours additional transition appeared at 61° C. that may indicate the beginning of the degradation process, i.e. formation of sebacic acid. Similar results were found for P(SA:RA) (2:8), before exposure of the polymer to buffer there is one transition that peaks at about 32° C. After 12 and 24 hours in buffer the transition temperature became 42° C. and 50° C., respectively.

Another observation made on polymers kept in the buffer is the polymer swelling capacity. It was found that P(SA:RA) (2:8) and P(SA:RA) (3:7) increased in their volume by 15% during first 24 hours in buffer.

Measurement of Viscosity

Cylindrical spindles were used. Polymers' viscosity was measured before the polymers were exposed to aqueous medium and after incubation for 12 hours in phosphate buffer solution (0.1 M, pH 7.4) at 37° C. with constant shaking (100 RPM). In order to obtain large enough sample to perform viscosity measurement the polymers were spread on a large surface and put into the buffer. After exposure to the aqueous medium the polymer sample was collected and put in the glass container. Temperature sensitivity test was performed starting at temperature of 40° C. and down to room temperature (22° C.) by applying constant rotational speed. Detection of Theological behavior was performed by measuring shear stress and/or viscosity at different shear rates, starting at 0.209 sec$^{-1}$, for more viscous polymers and up to 36 sec$^{-1}$ for a less viscous polymer. All experiments were performed in triplicates.

Figure 1:
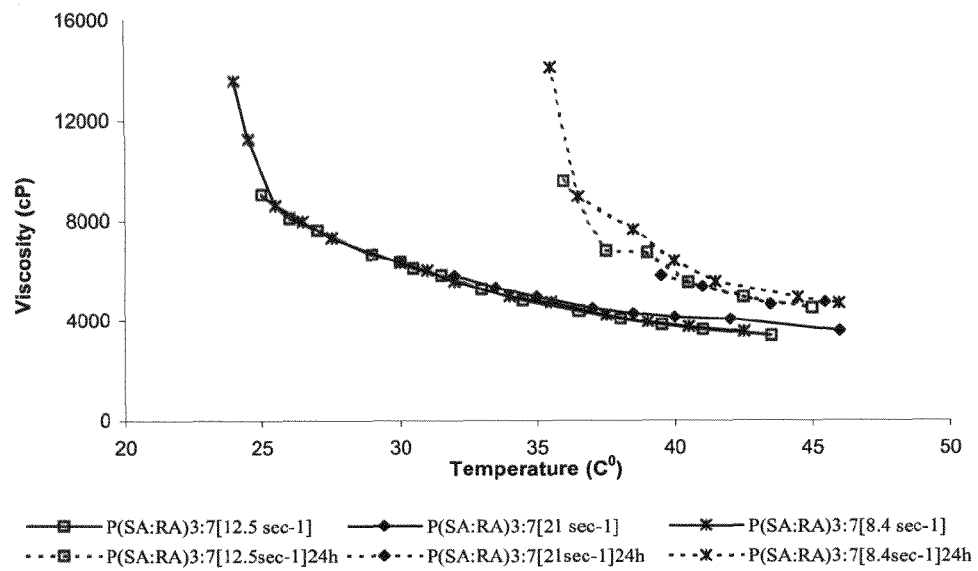
FIG. 1 is a graph showing the viscosities of p(SA:RA) 3:7 as a function of temperature (° C.) at different shear rates (shear rate applied is shown in brackets). The solid line shows the polymers before exposure to a phosphate buffer and the dashed line shows the polymer after exposure to a phosphate buffer ((pH 7.4, 0.1 M, 37° C. for 24 hours).

FIG. 1 shows the viscosities of the polymer P(SA:RA) (3:7) at three different shear rates (8.4, 12.5 and 21 sec$^{-1}$). The viscosity was measured starting at 43° C. to the lowest temperature it was possible to measure (25° C. in the case of P(SA:RA) (3:7). P(SA:RA) (3:7) shows properties of non-Newtonian fluid at lower temperatures (<30° C.), because of a non-constant shear rate/shear stress relationship and the polymer can be classified as a pseudoplastic shear thinning material displaying decreasing viscosity with increasing shear rate. This behavior is important for injectability of the polymer: as pressure is applied, the polymer paste becomes softer and pumped out through the needle. At higher temperatures (>30° C.), P(SA:RA) (3:7) acts as a Newtonian fluid and its viscosity is not affected by shear rate applied. The temperatures of greatest interest are room temperature (approximately 22-25° C., preferably 25° C.), because this is the temperature at which the polymer is injected, and the body temperature (37° C.), because this is the temperature to which polymer is exposed after the injection to the body. When shear rates of 8.4 sec$^{-1}$ and 12.5 sec$^{-1}$ were applied at room temperature, the viscosity of P(SA:RA) (3:7) prior to exposure to aqueous medium was 8600-9000 cP, while after the exposure to water, the viscosity was too high to be measured at room temperature at those shear rates. Increase in polymer viscosity after exposure to aqueous medium at 37° C. was dependent on the shear rate: for a shear rate of 8.4 sec$^{-1}$, the viscosity increased from 4200 cP to 8940 cP after exposure to buffer; at a shear rate of 12.5 sec$^{-1}$, the viscosity increased from 4360 cP to 6770 cP; and at 21 sec$^{-1}$ the viscosity increased from 4115 cP to 5765 cP. After exposure to the aqueous medium, the polymer shows a pseudoplastic behavior. This may be explained by reorganization of the polymer chains induced by the exposure to the buffer, which is destroyed at the moment of turning the spindle. The faster the rotation of the spindle (higher shear rate), the more the structure is destroyed and the less the structure molecules slide together, the lower the viscosity will be.

Figure 2:
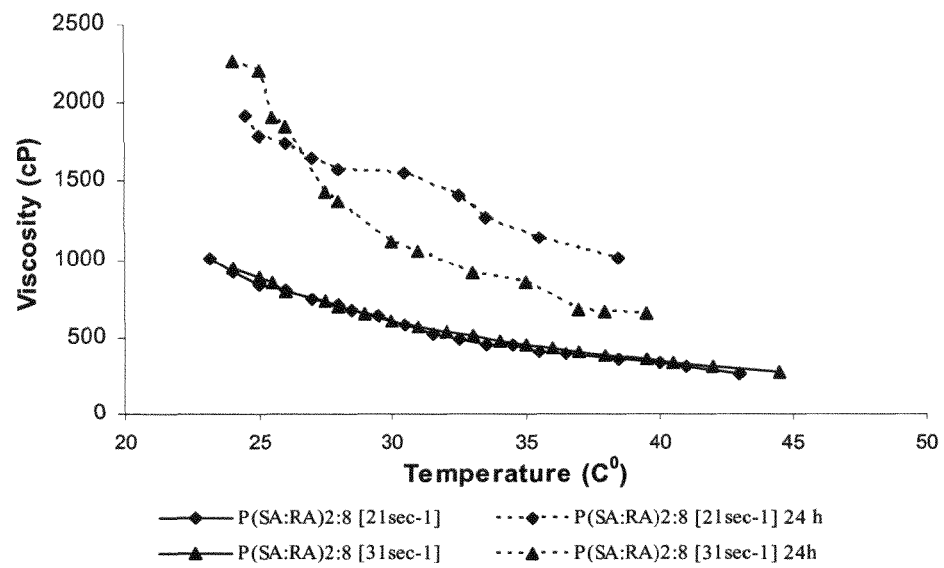
FIG. 2 is a graph of the viscosities of poly(sebacic acid-co-ricinoleic acid) (p(SA:RA)) (2:8) as a function of temperature (° C.) at different shear rates (shear rate applied is shown in brackets). The solid line shows the polymers before exposure to a phosphate buffer and the dashed line shows the polymer after exposure to a phosphate buffer ((pH 7.4, 0.1 M, 37° C. for 24 hours).

FIG. 2 shows the viscosities of the polymer P(SA:RA) (25:75) at three different shear rates (12.5, 21 and 31 sec$^{-1}$). The viscosity was measured starting at 43° C. to room temperature. P(SA:RA) (25:75) has a lower viscosity than P(SA:RA) 3:7, because of its higher content of ricinoleic acid that contributes to the liquidity of the polymer. P(SA:RA) (25:75) acts as a Newtonian fluid and its viscosity is not affected by shear rate applied in this range of temperatures. Because of the polymer's lower viscosity it was measured at higher shear rates. At room temperature at all shear rates applied (12.5, 21 and 31 sec$^{-1}$), the viscosity of P(SA:RA) (25:75) prior to exposure to aqueous medium was about 2900 cP, while after the exposure, viscosities were 8570 cP at 12.5 sec$^{-1}$, 5000 cP at 21 sec$^{-1}$ and too high to be measured at 31 sec$^{-1}$. The viscosity of P(SA:RA) (25:75) after exposure to aqueous medium when measured at 37° C. showed Newtonian fluid behavior, but there was still an increase in polymer viscosity by 2200 cP (1150 cP before exposure to buffer and 3200 cP after). In the case of P(SA:RA) (25:75), the polymer showed pseudoplastic behavior only when the viscosity was measured at room temperature, but not at 37° C.

The viscosities of P(SA:RA) (2:8) were measured at two different shear rates (21 and 31 sec$^{-1}$). P(SA:RA) (2:8) showed lower viscosity than that of P(SA:RA) (25:75), because of its higher content of ricinoleic acid (80%). P(SA:RA) (2:8) acts as a Newtonian fluid and its viscosity is not affected by shear rate applied in this range of temperatures. Because of the polymer's lower viscosity it was measured at higher shear rates. At room temperature at both shear rates applied (21 and 31 sec$^{-1}$), the viscosity of P(SA:RA) (2:8) prior to exposure to aqueous medium was about 900 cP, while after exposure, viscosities were 1800 cP at 21 sec$^{-1}$ and 1900 cP at 31 sec$^{-1}$. The viscosity of P(SA:RA) (2:8) after exposure to aqueous medium when measured at 37° C. also showed Newtonian fluid behavior.

Figure 3:
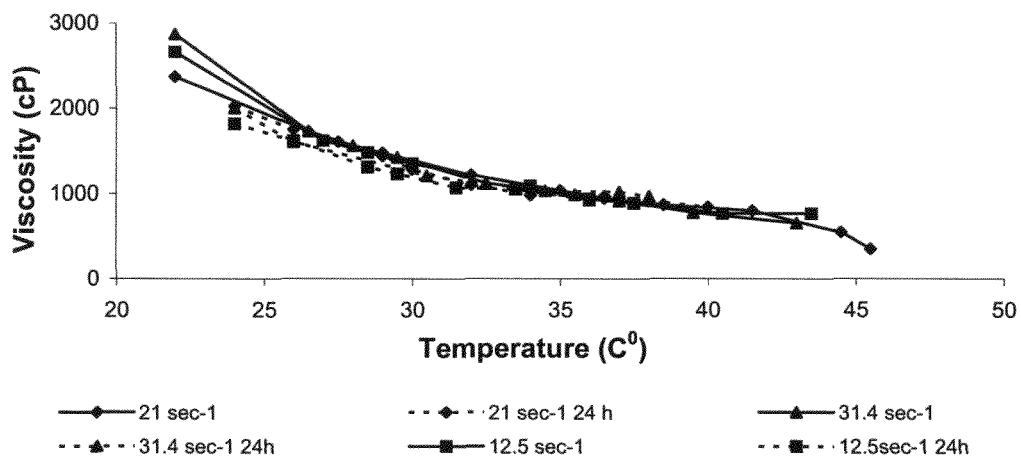
FIG. 3 is a graph of the viscosities of polyricinoleic acid (PRA) as a function of temperature (° C.) at different shear rates (shear rate applied is shown in brackets). The solid line shows the polymers before exposure to a phosphate buffer and the dashed line shows the polymer after exposure to a phosphate buffer ((pH 7.4, 0.1 M, 37° C. for 24 hours).

FIG. 3 shows the viscosities of the polymer poly(ricinoleic acid) (PRA) at three different shear rates (12.5, 21 and 31 sec$^{-1}$). PRA has similar viscosity to P(SA:RA) (2:8), but this polymer is liquid even at 4° C., does not change after contact with aqueous medium and acts more like an oil. PRA acts as a Newtonian fluid and its viscosity is not affected by shear rate applied in this range of temperatures.

The relationship between the shear stress (F) and the shear rate (dv/dr) is expressed mathematically in the Newton equation:

$$F = \eta dv/dr$$

where the proportionality constant, $\eta$, is the coefficient of viscosity.

FIG. 4 show the relationship between the shear rate and shear stress of the following polymers: P(SA:RA) (25:75), P(SA:RA) (2:8) and PRA before and after exposure to aqueous medium. The slope of the curve corresponding with P(SA:RA) (25:75) (FIG. 6a) that gelled in the aqueous medium is 23 times higher than before exposure to the aqueous phase. Concerning PRA, there was no change in polymer viscosity upon exposure to aqueous medium.

In Vivo Evaluation of Formulations

Inbred 8-10 week old female C3H mice, weighing about 20 g (Harlan Laboratories, Israel) were kept under specific pathogen free (SPF) conditions and given free access to irradiated sterile food and acidified water throughout the experiment. Different volumes of P(SA:RA) polymers (0.05.0.1 and 0.15 ml) were injected subcutaneously to the backspace via a 22G needle. 8 and 24 hours after injection, mice were sacrificed by cervical dislocation. The animal's skin was elevated and the polymer implant was exposed and photographed. Ethics committee at the Hebrew University in Jerusalem (NIH approval number: OPRR-A01-5011) has reviewed the application for animals' study and found it compatible with the standards for care and use of laboratory animals (ethics committee-research number: MD-80.04-3).

The mice injected with three different volumes of P(SA:RA) (3:7) (0.05.0.1 and 0.15 ml) before (12a) and after (FIGS. 5b and 5c) were sacrificed at 8 and 24 hours, respectively. At both time points, the injected implants maintained their shape and remain in the injection site, as it happens when oil is injected in the subcutaneous space. These in vivo experiments proved that polymer turned into gel in contact with tissue.

Additionally, the systemic and local effect of p(SA:RA) (3:7) implants in rats was observed for a period of 6 weeks. The p(SA:RA) was synthesized by melt condensation and a weight average molecular weight of 11,600. Female Spraque-Dawley (SD) rats were obtained from Harlan Lab. (Jerusalem, Israel). The rats' weight at implantation was 210±15.0 g. Rats were housed in the SPF unit of the animal facility and were allowed free access to food and water. Rats were randomly assigned to one of two groups (n=4): a control group, Group A, consisting of rats which received saline at the same injection-implantation sites and were anesthetized in the same way as the group receiving polymer implantations, and Group B, consisting of rats implanted with polymer matrices.

Each rat was removed from its respective cage and anesthetized using isotonic 5% chloral hydrate solution (0.64 ml/100 g) administrated through intraperitonal route. Each rat had been shaved using an animal clipper on the both dorsum sides and the femoral areas. Then the animals were prepared aseptically using 70% alcohol. The polymer implants were injected through 22 G needle subcutaneously on both sides of the each animal and intramusculary into the femoral muscle on both sides. The rats were allowed to wake-up in the operating room before they were returned to their cages.

At 5 days pre-implantation and the day of implantation blood samples were drown from the tail vein for determination the baseline parameters for each rat. At 3, 7, 21 and 42 days post-implantation rats were anesthetized and blood samples were drawn by cardiac punctuation. Samples were then analyzed (AML, Herzliya Pituah, Israel) for clinical chemistry and hematological parameters for each rat. The rats that received the polymer implant were divided into two groups.

The first group consisted of SD rats that received four injections of polymer blank. Two injections, 200 μl each, were subcutaneous on the opposite dorsal sides each. Two others, 50 μl each, were done intramuscularly in the femoral muscle of each leg. One implantation was used for biodegradation assessment, second implantation for histopathology evaluation. Organs of rats were selected randomly for evaluation of systemic toxicity.

The second group consists of Wistar rats received 10 μl of polymer blank intracranially. The polymer was injected through a hole in the cranium made over the left parietal region with its center 5.5 mm behind the coronal structure and 3.5 mm lateral to the sagittal structure. The injections were performed with 25 μl syringe and the deepness of needle insertion was 4 mm from the coronal surface.

At the 3, 7, 21 and 42 days post-implantation, the rats were anesthetized as described above, weighed and the weight of each rat was recorded. The rats were then sacrificed by cardiac puncture and autopsied. Gross observation of various organs and implantation sites were made at the time of autopsy. These organs were than removed, weighted, and fixed in buffered formaldehyde 4% (Biolab, Jerusalem, Israel). The tissues collected included: hart, brain, liver, spleen, lungs, thymus, and kidney. In addition, the local implant sites were removed and fixed in buffered formaldehyde 4%. All tissues were sectioned and stained with hematoxylin and eosin and examined microscopically.

During the autopsy, the polymer implant was removed, dissolved in chloroform, dried with anhydrous magnesium sulfate, filtered and the organic solvent was evaporated. The isolated residue was weighed and examined by IR for anhydride and ester content, GPC for molecular weight determination and NMR for RA to SA ratio. The aliquots of the degraded polymer matrix were hydrolyzed with 1 N aqueous KOH, acidified with concentrated HCl and the liberated oil residue was extracted with ethyl acetate. The organic layer was dried with anhydrous magnesium sulfate, filtrated and solvent was evaporated to dryness. The products of polymer hydrolysis were examined for content of ricinoleic acid and sebacic acid using HPLC.

The biocompatibility of each tissue was graded by 5 grades from excellent tolerance to intolerance as follows:

Excellent tolerance (No or minimal inflammatory reaction)
Good tolerance (minimal adverse reaction, minimal inflammation)
Moderate tolerance (moderate degree of inflammation)
Not good tolerance (adverse reaction, inflammatory reaction)
Intolerance (severe necrosis and inflammatory reaction)

All animals were healthy and gained weight similar to the control animals. No adverse effect or swelling was observed at the implant sites, while the injected polymer felt solid when touching the site. All organs separated from the animals of the study were normal and no difference was found among the control and the polymer groups. Histopathology of the injection/implant site tissues indicated an acute inflammation and some necrosis at the 3 day tome point with the adverse reaction confined top the injection site and tissues that are within mm from the polymer. At day 7, all implant sites showed minimal to moderate inflammation with significant improvement compared to day 3 sites. At day 21 and 42, excellent tolerability was detected. These histopathology results are similar to the results previously reported for the compatibility of the clinically used biodegradable polyesters and polyanhydrides.

With regard to brain compatibility, all animals in all time points, including the day 3 time point, presented excellent biocompatibility. Similar results were obtained from the paclitaxel loaded polymer.

The amount of polymer retrieved from the implant site was determined by gravimetric measurement after drying the samples. A gradual reduction in polymer content was found with almost total elimination by day 42 time point.

Conclusion

The results of this study prove that poly(sebacic-co-ricinoleic acid) described in this experiment gel upon interaction with water media and thus have a use in the in situ formation of polymer implant or use as biodegradable sealant or barrier to prevent tissue adhesion. These polymers are net materials with no solvent that form in situ an organogel. Organogels are composed of water-insoluble amphiphilic lipids, which swell in water and form various types of lyotropic liquid crystals. The nature of the liquid crystalline phase formed depends on the structural properties of the lipid, temperature and amount of water in the system. The amphiphilic lipids examined to date for drug delivery are primarily glycerol esters of fatty acids, such as glycerol monooleate, monopalmitostearate and monolinoleate that are waxes at room temperature. These compounds form a cubic liquid crystal phase upon injection into an aqueous medium. This liquid crystalline structure was gel-like and highly viscous. P(SA:RA) copolymers are water-insoluble copolymers which exhibit viscosity and melting point changes upon exposure to an aqueous medium. The rheological changes are caused by the formation of a three-dimensional network, and images obtained using SEM showed a reversible unique physical structure that appeared upon exposure to buffer. This three-dimensional structure may be explained by hydrogen bonding between the carboxylic groups and the surrounding water molecules. Similar mechanism was suggested for lecithin bridging by hydrogen bonds in the organogel, where lipid functional groups exhibit affinity for solvents and how they bound to them (Shchipunov Y A, Shumilina E V. Lecithin Bridging by Hydrogen-Bonds in the Organogel. Mater. Sci. Eng. C-Biomimetic Mater. Sens. Syst. 1995; 3(1):43-50).

Example 4

In Vitro and In Vivo Release of Paclitaxel from Poly(Sebacic Acid-Co-Ricinoleic Acid) Polymers in Mouse Bladder Tumors (MBTs)

The effectiveness of an injectable polymeric formulation, based on poly(sebacic acid-co-ricinoleic acid) and paclitaxel against a heterotropic tumor model was studied.

Methods and Materials

Poly(sebacic acid-co-ricinoleic acid ester anhydride) 2:8 was synthesized as discussed above. Paclitaxel GMP grade (BioxelPharma, QC, Canada), acetic anhydride (Merck, Darmstadt, Germany), and Lutrol F68 (Sigma, Israel) were used. All solvents were analytical grade from BioLAB (Jerusalem, Israel) or Frutarom (Haifa, Israel) and were used without further purification. The MBT (mouse bladder tumor) cells were a generous gift from Dr. Ofer Gofrit from Hadassah Ein-Karem Hospital (Jerusalem, Israel). Cell culture medium and fetal calf serum (FCS) were obtained from Beit-Haemek (Israel).

The molecular weight of the poly(ester-anhydride) was estimated on a gel-permeation chromatography (GPC) system consisting of a Waters 1515 isocratic. HPLC pump with Waters 2410 refractive index (RI) detector, a Rheodyne (Coatati, Calif.) injection valve with 20-αL loop (Waters Ma). Samples were eluted with chloroform through a linear Ultrastyrogel column (Waters; 500 Å pore size) at a flow rate of 1 mL/min. The molecular weights were determined relative to polystyrene standards (Polyscience, Warrington, Pa.) with a molecular weight range of 500-10000 using a Breeze computer program. Paclitaxel concentrations in buffer solutions were determined by high-performance liquid chromatography (HPLC [Hewlett Packard, Waldbronn, Germany]) system composed of an HP 1100 pump, HP 1050 UV detector, and HP ChemStation data analysis program using a C18 reverse-phase column (LichroCart® 250-4, Lichrospher® 100, 5 μm). A mixture of 65% acetonitrile: 35% water at a flow rate of 1 ml/min was used as eluent and UV detection was performed at 230 nm.

Paclitaxel content in the polymer matrix was determined by a normal phase HPLC system composed of a Purospher® STAR Si analytical HPLC column (250×4 mm, particle size 5 μm) was used with a Purospher® STAR Si guard column (4×4 mm, particle size 5 μm) (Merck, Darmstadt, Germany) at ambient temperature (25+10° C.). The mobile phase consisted of dichloromethane (DCM) and methanol (MeOH) at different ratios (1%-2.5% v/v). An isocratic mode of elution was utilized with a flow rate of 1 ml/min. UV detection was performed at two wavelengths, 240 nm and 254 nm (Vaisman et al., 2005).

Preparation of Formulations and In Vitro Drug Release

Formulations of polymer loaded paclitaxel (5% and 10% w/w) were prepared by direct mixing of the polymer with the drug at room temperature. The composition was mixed until a smooth paste was formed. All formulations were filled in syringes at room temperature without heating. The obtained formulations were injectable semi-solid pastes at room temperature. In vitro drug release studies were conducted by injecting 10 mg of the pasty formulation sample in a 50 ml phosphate buffer solution (0.1 M, pH 7.4) at 37° C. with constant shaking (100 RPM). The paste hardened to a soft solid shortly after addition to the buffer. The release medium was replaced periodically with fresh buffer solution and paclitaxel concentration in the solution was determined by HPLC. All experiments were performed in triplicate.

In Vitro Hydrolytic Degradation

The in vitro hydrolysis was evaluated by injecting 25 mg of the blank polymer P(SA:RA) (2:8) or formulation containing paclitaxel (5 and 10%, w/w) in phosphate buffer solution (50 ml, 0.1 M, pH 7.4) at 37° C. with constant shaking (100 RPM). The medium was replaced periodically with fresh buffer solution. At each time point, the polymer sample was taken out of the buffer, weighed wet and dry after lyophilization. The hydrolysis of the polymer was monitored by (1) molecular weight decrease and (2) paclitaxel content in the remaining polymer formulation. At each time point the formulation was examined for paclitaxel content in the degraded sample by NP HPLC.

In Vivo Degradation of Formulations

Inbred 8-10 week old female C3H mice, weighing about 20 g (Harlan Laboratories, Israel) were kept under specific pathogen free (SPF) conditions and given free access to irradiated sterile food and acidified water throughout the experiment. Blank polymer and pasty formulations containing paclitaxel (5% and 10% w/w) were injected subcutaneously to the backspace via a 23G needle into 12 groups of four C3H mice in each group. The animals were observed for signs of local and systemic toxicity and for weight loss. After 1, 7, 21 and 70 days, mice were sacrificed by cervical dislocation. The polymer implant was taken out, weighed before and after lyophilization and examined for paclitaxel content in the remaining formulation. The ethics committee at the Hebrew University in Jerusalem (NIH approval number: OPRR-A01-5011) reviewed this study and found it compatible with the standards for care and use of laboratory animals (ethics committee-research number: MD-80.04-3).

In Vivo Anti-Tumor Activity

Inoculation of MBT Cells

Inbred 8-10 weeks old female C3H mice, weighing about 20 g (Harlan Laboratories, Israel) were kept under specific pathogen free (SPF) conditions and given free access to irradiated food and acidified water throughout the experiment. Mice were injected subcutaneously via a 27-gauge needle in the posteriolateral flank with 1*106 MBT cells suspended in 0.1 ml RPMI medium. Tumors were measured using caliper every other day and their volumes were calculated using the following formula, which is described in the literature:

length×width×height×0.523

Treatment Protocols

In the MBT model, the treatment was initiated 8 days after inoculation, when the tumor was palpable and reached 0.5 cm$^3$. The mice were randomly assigned to one of the three treatment groups (n=10 in each group). The two control groups (n=10 in each group) received intratumoral injection of 0.1 ml of the blank polymer or no treatment at all. The first treatment group was injected with 0.1 ml of a formulation containing 5% paclitaxel (equivalent to 250 mg/kg) intratumorally, the second treatment group received 0.15 ml of this formulation (equivalent to 375 mg/kg) and the third group received 0.15 ml of a formulation containing 10% paclitaxel (equivalent to 750 mg/kg). Mice were injected only once during the experiment. The animals were sacrificed when the tumor became ulcerated or when it caused unacceptable discomfort.

Results and Discussion

In Vitro Paclitaxel Release

The polymer carrier-random Poly(SA:RA) 2:8 of Mw=4000 and Mn=3500 was prepared from purified RA, 98% pure and SA 99% pure by melt condensation as discussed above. The structure of the polymer is shown below.

results are shown in FIG. 6. The polymer without paclitaxel had the fastest rate of degradation. In the first week the blank polymer lost 33±2% of its initial weight, then gradually degraded and after 40 days it lost 90.7±6.8% of its initial weight. The degradation rate of the polymer loaded with paclitaxel was slower. The formulation containing 5% paclitaxel degraded during the first week by 18±5%, after 40 days it lost 78±4% and after 80 days only 6% of the formulation was left. The formulation containing 10% paclitaxel degraded during the first week by 13±5%, after 40 days it lost 65±8% and after 80 days 19% of the formulation left. The molecular weight (Mw) decrease of the blank polymer and polymer containing paclitaxel was similar. After the samples were immersed in the buffer their Mw dropped from 3900 Da to 1200 Da during the first three days. During the next 25 days the molecular weight of the blank polymer dropped to 670 Da, while the formulations with paclitaxel kept their Mw at 1070 Da, which is mainly paclitaxel contribution. Slower degradation rate of polymer containing paclitaxel support our earlier finding that paclitaxel protects the polymer and does not allow water to penetrate, dissolve the drug and polymer degradation products. On the other hand the Mw of the formulation decreases almost as the Mw of the blank polymer. This means that water still can penetrate inside the polymer matrix and cause hydrolysis of the polymer.

The weight loss of the formulations containing paclitaxel is faster than the paclitaxel release rate. The Formulation containing 5% paclitaxel lost 78% of its initial weight after 40 days (FIG. 6a), while releasing only 35% of the incorporated drug (FIG. 6b). The same disproportion was found for the

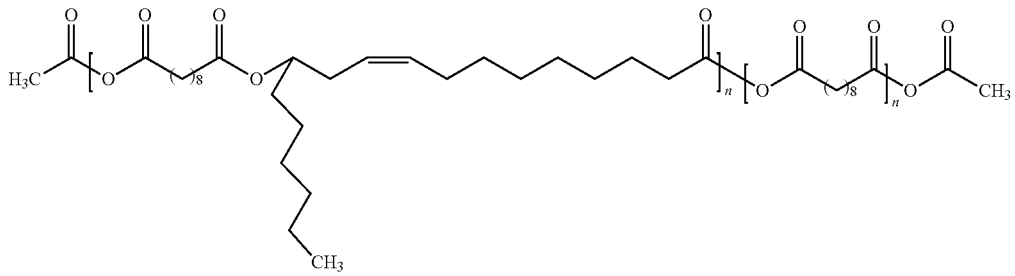

Paclitaxel was incorporated in the polymer (5% and 10% w/w) without affecting the molecular weight of the polymer or chemically interacting with the polymer, as confirmed by GPC and $^1$H-NMR. FIG. 5 shows the release profile of 5% and 10% paclitaxel from P(SA:RA) 2:8. The Formulation that contained 5% paclitaxel released 20±1.4% of the incorporated drug over 20 days, while formulation containing 10% released 8±0.8%. The release profile was monitored for 60 days. During this period the formulation that contained 5% paclitaxel released 40±0.5% of the incorporated drug, while the formulation containing 10% released 16±0.3% of its content. Sink conditions were kept during the release study and paclitaxel concentration in the releasing medium was no higher than 10% of its maximal solubility in buffer (solubility in buffer is approximately 5 µg/ml). Because of the hydrophobic nature of paclitaxel, its release rate from the polymer is a function of the amount of drug loaded in the polymer: the higher the loading of paclitaxel, the slower the rate of its release.

In Vitro Hydrolytic Degradation

We studied the hydrolysis of the polymer by monitoring the molecular weight and the decrease in sample weight. The 10% formulation: after 20 days it lost 27% of its initial weight (FIG. 6a), while only 8% of the incorporated drug was released (FIG. 6b). These results correlate with the paclitaxel accumulation in the degrading formulation (FIG. 6b). After 7 days in the degradation medium the paclitaxel content in the formulation rose by 15±3.5%, after 15 days by 52±13% and after 40 days the paclitaxel content was almost twice its initial value (raised by 98±15%). As stated earlier: higher paclitaxel content caused slower paclitaxel release, but the polymer matrix could still be degraded.

In Vivo Degradation of Formulations

The degree of the in vivo degradation of the injected formulations was evaluated by weight loss (FIG. 7). The blank polymer lost 40±7% of its initial weight after one day in vivo, P(SA:RA) (2:8) loaded with 5% paclitaxel lost 31±5% and P(SA:RA) (2:8) loaded with 10% paclitaxel lost 15±8%. The blank polymer completely degraded seven days post injection, while formulations with paclitaxel lost half of their initial weight by that time (no significant difference was seen between formulations containing 5% or 10% paclitaxel) and they were totally eliminated from the site of injection after 70 days. No evidence of any active inflammatory reaction or tissue irritation at the injection site of the formulation containing paclitaxel was noted.

In Vivo Anti-Tumor Activity

The efficacy of paclitaxel delivered intratumorally was investigated in the mouse bladder tumor (MBT) heterotrophic model. The treatment was initiated on the eighth day after tumor cell inoculation. Mice that were not treated and mice injected with the blank polymer were sacrificed 25 days after inoculation because the tumor size exceeded 17 $cm^3$. However, the dimensions of the tumor were smaller in the blank injected group (11 vs. 17 $cm^3$ of the control untreated group) (FIG. 8). It is theorized that injection of the blank polymer into the tumor damaged its structure and delayed its development.

The best results for survival and tumor size were seen in the group treated with the 0.15 ml of formulation containing 5% paclitaxel (100% survival, all mice were alive 30 days post tumor cells inoculation) and in the group treated with 0.15 ml of formulation containing 10% paclitaxel (75% survival). Survival of 60% and 50% was in the group treated with 0.1 ml of formulations containing 5% and 10% paclitaxel, respectively.

The progression of tumor growth in mice is shown in FIG. 8. In all treatment groups (0.1 ml, 0.15 ml of formulation containing 5% paclitaxel, and 0.15 ml of formulation containing 10% paclitaxel) the tumor size was 4 times smaller than that in the group treated with blank polymer and 5 times smaller than in group without treatment. This difference is statistically significant ($p<0.001$, t-student test). This was confirmed by visually inspecting the untreated mouse and the mouse that was treated 20 days post tumor inoculation The poly(sebacic co-ricinoleic acid) (2:8) used in this study is a hydrophobic polymer, built of natural fatty acids, which may be used for release of both, hydrophobic and hydrophilic drugs. The purpose of this study was to evaluate the effect of paclitaxel-polymer formulation injected intratumorally in heterotrophic model in mice. The polymeric paste formulation with paclitaxel is a viscous liquid at room temperature, that may be injected through a 23-gauge needle and it gels in contact with body fluids. This formulation formed a semi-solid implant in situ that released the drug locally at the site of injection.

For all formulations, the in vivo degradation and release were much faster than the in vitro, because one in vivo there is an efficient elimination of the fatty degradation products from the injection site while under in vitro conditions, the fatty degradation products remain and block the degradation process and drug release.

Example 5

In Vitro and In Vivo Release of Paclitaxel from Poly(Sebacic Acid-co-Ricinoleic Acid) Polymers in Melanomas Local delivery of paclitaxel from the formulations injected intratumorally was investigated using a melanoma heterotropic model in C57BL/6 mice. Changes in tumor progression, survival time and body weight were observed over a period of 77 days to determine the effectiveness of the local paclitaxel treatment. Tumor bearing animals were injected intratumorally with different volumes of formulation containing 5%, 10%, 15% and 20% paclitaxel.

The controlled-release formulation were prepared with a biodegradable polymer poly(sebacic acid-co-ricinoleic acid) (p(SA:RA)) at ratio of 20:80. The polymer P(SA:RA) 20:80 was mixed with paclitaxel (Bioxel Pharma, Sainte-Foy, Canada) at 5%, 10%, 15% and 20% w/w loading. The mixture was prepared at room temperature by triturating and then was drawn up into 1 ml Luer lock syringes, capped with 23G needles and stored at $-200°$ C. until use. Control polymers (without the drug) were also loaded in the 1 ml Luer lock syringes. Paclitaxel suspension for intratumoral injection was prepared by mixing 100 mg paclitaxel with 200 mg Pluronic F-68 (at a ratio 1:2) and adding 700 µl saline.

Female C57BL/6 mice (20-21 g) were obtained from Charles River Canada, St-Constant, Qc. B16F1 murine cells lot no 1511548 p32 (CRL-6223) were a generous gift of Dr. Michel Pagé. The cells were originally obtained from the American Type Culture Collection. The research protocol #2004-070 was accepted by the Secrétariat local de protection des animaux is located at University Laval, Pavillon Agathe Lacerte, local 1040, Sainte-Foy, (Québec) Canada, G1K 7P4. Requests are examined individually based on the guidelines provided by the Canadian Council on Animal Care (CCAC).

Inoculation of B16F1 Cells.

Once the animals were acclimatized to their environment and before the grafting of the tumors the mice were separated into 8 groups of ten (10) mice (111 mice in group control #8) where the inter groups mean body weight of mice was as equivalent as possible. Mice were injected subcutaneously at the level of the shoulder blade with 200 000 B16F1 tumor cells in suspension in 100 µL of DMEM. The mice were observed twice a day, morning and evening; they were weighed daily and tumors were measured every day since they were growing rapidly. At the moment where the melanoma tumors were detectable their measurement was initiated. Tumor volume was estimation was based on the standard formula: Tumor volume $(mm^3)=(w^2 \times l)/2$ where w=width and l=length in mm of the tumor. The experiment was continued and the mice were sacrificed when the tumor weight had reached 10% of the body weight or when discomfort, as described in the ethics protocol, became unacceptable. Mice meeting the criteria for euthanasia were sacrificed using $CO_2$. Following euthanasia, the lungs were recovered and the number of lung metastasis was determined visually. A brief autopsy was carried out to determine the presence of metastases.

Treatment Protocols

Two days after tumor grafting mice received their treatments. The two negative control groups (n=10 in each group) were injected intratumorally with 0.1 ml of the polymer P(SA:RA) (20:80) without paclitaxel (group #1) and group #8 received no treatment at all. The treatment groups 2-5 were injected intratumorally with polymer P(SA:RA) (20:80) loaded with 5%, 10%, 15% and 20% paclitaxel (0.2 ml for 5% and 10% loading and 0.1 ml for 15% and 20% loading). The treatment group 6 was injected intratumorally with paclitaxel suspension loaded with 10% paclitaxel (0.1 ml). Mice were injected only once during the experiment. The treatment group 7 was treated with the traditional systemic treatment of paclitaxel/Chremophor solution injected intraperitonial on days 1, 4, 7 and 10. The animals were sacrificed when the tumor became ulcerated, when it caused unacceptable discomfort or when tumor size had reached 10% of the animal weight.

Statistical Analysis

All statistical analyses were performed using S-PLUS. The survival time, in days, was recorded for each mouse. Non-parametric survival curves by treatment group were obtained using the Kaplan-Meier method, taking into account the right-censored cases (for animals living beyond the end of the study). To test whether there is a statistically significant difference in survival time for animals receiving the Paclitaxel gel treatments, survival curves were compared using a log-rank test. A related measure of survival is the hazard ratio between two treatments. The hazard provides the rate of death during a small unit of time or a measure of the incidence rate of dying during the next subsequent time interval. To estimate the hazard ratios between the treatments versus the placebo, a semiparametric Cox proportional hazards regression model was fitted to the data. To quantify the effect of Paclitaxel dose concentration on the hazard ratio and take into account the increasing concentration level of Paclitaxel within the five gel treatments, a Cox proportional hazards model was fitted for the five gel treatments. Specifically, we wish to model the effect of dose, as a continuous variable, on the hazard ratio. Moreover, to account for any curvature in the relationship between dose and the hazard ratio, a squared term for dose was also included in the model. More precisely, the fitted model was:

Should the quadratic term Log(Hazard Ratio)= $a*Dose+b*Dose\ 2$ appear statistically significant in the model, the optimal dose concentration between 0% and 20% providing the smallest hazard ratio can be determined by finding the minimum of the curve, if a minimum exists.

A global significance level of $\alpha=5\%$ was assumed for all statistical tests.

For each statistical test, whenever an overall treatment effect was found, multiple comparison methods were used to qualify which pairs of treatments are statistically different. To account for multiple testing, a multiple comparisons correction was applied using the Tukey method to maintain the global $\alpha$-level at 5%. Non-parametric survival curves for the time until detectable tumor volume by treatment group were obtained using the Kaplan-Meier method, taking into account the right-censored cases (animals with consistent tumor volumes of 0).

Results and Discussion

As aforementioned, the average weight of each group on the day of treatment ranged from 20 grams. The inter groups average weights distribution was very narrow during the first ten (10) days post treatment. After the first ten (10) days of the experiment, the weight increase was relatively similar for each group and showed no correlation with the type of treatment since the euthanasia of mice having significant tumor weight "equilibrated" for the increase of weight of the remaining tumors.

The p-value of 0.8993 indicates that there is no statistically significant of the treatment received on relative body weight, at an $\alpha$-level of 0.05. This provides formal evidence to support the observations made from the descriptive statistics presented that relative body weight is not affected by the treatment received.

The effect of time alone did have a statistically significant influence on body weight with a p-value less than 0.0001. This is consistent with the graphs, where we see an increase in body weight over time.

More importantly, however, is to assess whether the change in body weight over time depends on the treatment received. In other words, whether the interaction, Treatment*Day, is significant. From the ANCOVA table, we see that the interaction was not found not to be statistically significant, with a p-value of 0.4151. This implies that the effect of time on relative body weight does not vary by treatment group.

Rate of Survival of Animals

The rate of survival for each group is shown in FIG. 9. Survival was the lowest among group #8, which was the control group, which did not receive any form of treatment and also in group #1 which received polymer P(SA:RA) (20:80) alone without paclitaxel. For both groups animal death started on day 13 and mice were all dead on day 20 with a median survival time (MST) of 16 days. All mice that have received paclitaxel in their treatment exhibited MST higher than controls illustrating the non-acute toxicity of the treatments.

Groups treated with a polymer P(SA:RA) (20:80) the MST were 16, 22, 35, 18 and 20.5, respectively for concentration of paclitaxel of 0, 5, 10, 15 and 20%, respectively. Finally, mice treated with paclitaxel/Pluronic F68 suspension and the commercially available paclitaxel (in saline) for IP administration the MST were 18 and 19 days respectively. Interestingly, group #6 (paclitaxel/Pluronic F68 suspension) exhibited a "bimodal" death curve. Indeed, the 6 first mice of the group died quickly while the remaining 4 had a significantly increased survival. Table 4 summarizes the treatments and the corresponding MST for all groups.

TABLE 4

Summary of the treatments effect on mice survival

| Group | Formulation mixture | Paclitaxel (%) | Median Survival Time (days) |
|---|---|---|---|
| 1 | P(SA:RA) (20:80) | 0 | 16 |
| 2 | P(SA:RA) (20:80) | 5 | 22 |
| 3 | P(SA:RA) (20:80) | 10 | 35 |
| 4 | P(SA:RA) (20:80) | 15 | 18 |
| 5 | P(SA:RA) (20:80)0 | 20 | 20.5 |
| 6 | *Paclitaxel/Pluronic F68 | 10 mg/0.1 mL | 18 |
| 7 | (Ethanol 49.7%-Chremophor EL) diluted in saline | *Paclitaxel (20 mg/Kg, 0.4 mL of solution was administered) on D1, D4, D7 and D10 | 19 |
| 8 | None | No drug administered | 16 |

A correlation between the amount of paclitaxel injected and survival could not be clearly established. However the efficacy of paclitaxel loaded and delivered in polymer P(SA:RA) (2:8) on the survival is conspicuous. Indeed, in the untreated groups none of the mice survived (maximal survival time was 23 days) while in the treated groups and after 77 days there are very healthy mice in 5 groups (group #3=3 mice; group #4=1 mouse; group #5=1 mouse)

A log-rank test was performed across all treatment groups to determine whether there was an overall effect of treatment on survival time. The statistical test revealed a highly significant effect of treatment on survival time with a chi-squared value of 32 and a p-value of 0.00004.

To determine which pairs of treatment were statistically different, log-rank tests were performed on all pair combinations of treatment. A Tukey (Honestly Significant Difference) adjustment was applied for multiple comparisons to ensure a global $\alpha$-level of 5% was maintained. Under this method, the corrected $\alpha$-level for each comparison was 0.002, or 0.2%.

Table 3 reports the p-values of the log-rank tests. Values in bold marked by a star, where the p-value is less than 0.002, indicate pairs of treatments found to have a statistically different survival distribution. Of the four polymer loaded paclitaxel treatments, only the 5% and 10% concentrations were deemed to have statistically different survival curves from the placebo. Moreover, the 10% and 20% dose concentrations differ significantly from the 0% concentration, the treatment group most resembling the placebo control group. Within the 5% to 20% active Paclitaxel gel treatments, no differences in survival were detected. In summary, statistically significant differences were found solely between active treatments (10%, 20% gel treatments) and non-active treatments (0% gel treatment and placebo).

Tumor Growth

The rate of tumor growth for each group after treatment is shown in FIG. 10. The highest tumor size is reported for the control groups that did not receive paclitaxel in their treatment regiment. In group #8 (no treatment) the tumor size was 3.6 g on day 20, in the group #1 (P(SA:RA) (20:80) without paclitaxel) the tumor size was 2.5 g. In all groups treated with polymer loaded with paclitaxel the tumor size was much smaller than that in the blank polymer or non treatment groups and ranged from 1.3 g to 0.3 g (FIG. 11).

From this data, we can observe that
- Active treatments exhibited longer latency periods than the placebo or 0% Paclitaxel treatments, that is, the time before tumor size begins to increase
- The Paclitaxel—polymer treatments at 5%, 10%, 15% and 20% seem to have a slower rate of increase in tumor volume than the other treatments
- Mice with undetectable tumor growth are observed for the Paclitaxel polymer treatments at 5%, 10%, 15% and 20% as well as the Paclitaxel/Pluronic F68 Treatment The descriptive statistics on the time (in days) before a detectable tumor volume shows that:
- The majority of mice with continually undetectable tumor volumes occurred in the 10% Paclitaxel gel treatment group
- The highest median time, i.e. 26.5 days, occurred with the 10% dose as well
- The coefficient of variation (CV) is lower in the placebo and 0% dose groups than in the active treatments
- This can be explained by the fact that the animals tend to react differently within the active treatment groups; whereas the behavior in the control groups is more consistent Consistent with the survival curves the 10% paclitaxel gel treatment appears to outperform the other treatments in providing the longest survival time. Again, the placebo control and the 0% Paclitaxel gel treatment correspond to the steepest survival curves, implying a rapid decent in the probability of zero tumor growth over time.

To compare treatments, a Cox proportional hazards model was fitted to test the effect of treatment on the hazard. The estimated hazard ratios are presented in the output below with reference to the placebo control. From the output, we find that the hazard ratio between each treatment and the placebo is statistically significant (p-values<0.05). As is consistent with other results, the treatment exhibiting the highest reduction in hazard is the 10% Paclitaxel gel treatment with a hazard of 0.0338 times that of the placebo. Moreover, the 5% and 15% Paclitaxel gel treatments provide a similar reduction in the hazard of developing a detectable tumor volume, with hazard ratios of 0.0933 and 0.0907 times that of the placebo.

Loss of body weight after treatment was shown in none of the groups. This is an important indication of the low toxicity of the treatment and shows that at least 100 microliters of a 20% paclitaxel formulation (Group 5, 20 mg paclitaxel), can be injected. Animals were healthy at the time of treatment as indicated by a constant increase in body weights in the 10 days after treatment. Body weights kept increasing steadily in all groups after treatment. However, the skin ulceration of the skin of mice treated with the gel containing paclitaxel clearly demonstrated a significant local toxicity. That toxicity may be associated to the pressure exerted by the polymer on the surrounding tissues, which are becoming less irrigated by the blood vessels, therefore increasing at the toxic level the drug locally.

In spite of the ulceration problem encountered with the gels containing paclitaxel it is clear that the pharmaceutical formulation had a significant beneficial effect on mice survival, for example 30% of the mice of group #3 treated by paclitaxel 10% in polymer P(SA:RA) (20:80) are still surviving after 77 days while none survived more than 23 days in control groups. Interestingly, no systemic toxicity was observed. The correlation of survival and drug concentration is not as nice as expected but the local toxicity observed in mice treated by the gel formulation might have to be accounted for. Another reason for the lack of correlation between survival and dosage in treated groups could be related to the fact that the selected tumor model used in the study is a relatively fast growing tumor as compared to the slow drug release by the formulation. A slower growing tumor model may be a better representation of clinical treatment.

Polymer Appearance

Interestingly, it was observed at the moment of the first necropsy that the polymer in the vicinity of the tumor had very similar appearance than the one injected. However, few days later the polymer seemed to harden and the masses were shrinking. In addition, the tissues surrounding the polymer loaded with paclitaxel was transforming, degraded.

Example 6

In Vitro and In Vivo Release of Paclitaxel from Poly(Sebacic Acid-co-Ricinoleic Acid) Polymers in Prostate Adenocarcinoma The objective of this study was to evaluate the efficacy of an injectable polymeric paste formulation with paclitaxel against orthotopic prostate tumor in rats. The polymer loaded with paclitaxel was injected at room temperature into the tumor bearing prostate glands of the rats three days after tumor cell inoculation. The Dunning R-3327 rat prostate adenocarcinoma is the corresponding experimental tumor model of its human counterpart used to study tumor progression. In our study we used the MatLyLu subline, which has the most aggressive local and metastatic potential.

Poly(sebacic acid-co-ricinoleic acid ester anhydride) (2:8) was synthesized as previously described. Paclitaxel GMP grade (BioxelPharma, QC, Canada), acetic anhydride (Merck, Darmstadt, Germany), Lutrol F68 (Sigma, Israel), and Chremophor EL 50% (Sigma, Israel) were used. All solvents were analytical grade obtained from BioLAB (Jerusalem, Israel) or Frutarom (Haifa, Israel) and were used without further purification.

On the day of injection, tumor cells (Dunning tumor, subline MatLyLu) were removed from the tissue culture flasks with trypsin/EDTA. After trypsination of the cells (1 min), 4 ml RPMI 1640 was added. The tumor cells were centrifuged, washed twice in PBS, counted and resuspended in RPMI 1640 medium without supplements at three final concentrations: $1\times10^5$, $3\times10^5$ and $5\times10^5$ viable tumor cells/ml.

Male Copenhagen rats (n=12) with a starting body weight of 220-240 g (Harlan Laboratories, Israel) were kept under specific pathogen free (SPF) conditions and given free access to irradiated sterile food and acidified water throughout the experiment. For creation of the orthotopic model the Copenhagen rats were divided in three groups and anesthetized (ketamine/xylasine, IP). The lower abdomen shaved, and a transverse incision made above the pubic bones. The abdominal muscles were divided, the intestine lifted up and the ventral lobe of the prostate exposed inferior to the bladder. Different numbers of MatLyLu cell suspended in 50 µl were injected into the ventral lobe using a 1 ml insulin syringe and a 26G needle as follows:

Group 1: 8×103 cells suspended in 50 µl RPMI 1640 medium;
Group 2: 1.5×104 cells suspended in 50 µl RPMI 1640 medium;
Group 3: 2.5×104 cells suspended in 50 µl RPMI 1640 medium;

The abdominal muscles were closed with 3/0 vicryl suture, and the skin with 3/0 silk. Three days later (as obtained from the preliminary studies) the rats were sacrificed. Histopathology evaluation of their prostate, liver and lungs was done to determine the presence and the degree of the tumor development.

Formulation Preparation

Formulations of polymer loaded paclitaxel 10% w/w were prepared by direct mixing of the polymer with the drug at room temperature. The composition was mixed until a smooth paste was formed. All formulations were filled in syringes at room temperature without heating. The obtained polymer formulations were injectable pastes at room temperature.

Suspensions of paclitaxel were prepared by mixing paclitaxel with Pluronic F68 at ratio 1:2 and then the mix was dispersed in saline to obtain paclitaxel concentration of 7.5% w/v. Pluronic F68 is a suspending agent used to suspend low water solubility agents, like paclitaxel. Each rat was injected intratumorally with 250 µl of the suspension.

For preparation of the parenteral solution of paclitaxel, the drug was dissolved in ethanol 50%/Chremophor EL50% to obtain paclitaxel concentration of 6 mg/ml. Then the solution was diluted with saline to obtain a solution of 1.2 mg/ml paclitaxel. Each rat was injected IP with 4 ml of the diluted solution.

Tumor Inoculation and Treatment

Male Copenhagen rats (n=26) with a starting body weight of 220-240 g (Harlan Laboratories, Israel) were kept under specific pathogen free (SPF) conditions and given free access to irradiated sterile food and acidified water throughout the experiment. For creation of the orthotopic model the Copenhagen rats were divided in five groups and anesthetized (ketamine/xylasine, IP) and operated as indicated above. Tumor cells (8×103 MatLyLu cells suspended in 50 µl) were injected into the ventral lobe using an insulin syringe and a 26G needle as follows. The abdominal muscles were closed with 3/0 vicryl suture, and the skin with 3/0 silk. The animals' body weight was monitored every 2 days. The therapy was started three days after tumor cells injection. The polymer loaded with the drug and the paclitaxel suspension were injected into the growing tumor in the ventral lobe of the prostate. Rat in the group treated with the parenteral paclitaxel were injected IP every three days. The experiment timetable is described in Table 5 and the treatment groups are described in Table 6.

TABLE 5

Summary of Experiment Timetables

| Day | Treatment | Comment |
| --- | --- | --- |
| 0(D0) | Implantation of the Mat-LyLu tumor cells (8*10³/50 µl) | Rats were anesthetized with (ketamine/xylasine, IP) and tumor cells suspended in 50 µl medium were injected in the prostate |
| 3(D3) | Administration of various treatments | |
| 4(D4-D35) | Rats are visited every day | Rats are weighted daily |

TABLE 6

Summary of Treatment Groups

| Group | Number of rats | Formulation | Injection volume/ Paclitaxel amount per rat | Comments |
| --- | --- | --- | --- | --- |
| 1 | 5 | No treatment | — | |
| 2 | 5 | *Paclitaxel/ Pluronic F68 | 250 µl/ 20 mg | Intratumorally, one treatment |
| 3 | 5 | P(SA:RA)2:8 + 10% paclitaxel | 200 µl/ 20 mg | Intratumorally, one treatment |
| 4 | 4 | **Paclitaxel in Ethanol 50%-Chremophor EL50% diluted in saline | 4 ml/ 4.8 mg (aprox. 20 mg/kg) | IP, three treatments every 3 days |

The animals were observed for signs of systemic toxicity and for weight loss. The ethics committee at the Hebrew University in Jerusalem (NIH approval number: OPRR-A01-5011) has reviewed this study and found it compatible with the standards for care and use of laboratory animals (ethics committee-research number: MD-80.04-3).

Macroscopic Tumor Calculation

After harvesting from the animal, the tumor was resected and a macroscopic calculation of the tumor volume was conducted using the formula shown below:

$$V = (length \times height \times width) \times \pi/6.$$

Histological Analysis

The tumors from all animals were resected, measured and fixed in 4% formaldehyde solution. The tissue slides were processed into paraffin and 3-µm sections were stained with hematoxylin & eosin for histological evaluation. The examination parameters were necrosis total area, capsule formation, inflammatory cell infiltration and content of intratumoral blood vessels.

Statistical Analysis

Survival distributions and median survival were calculated by the Kaplan-Meier method, and were compared using the log-rank test. P values less than 0.01 were considered significant for all tests.

Results and Discussion

The surgical procedure and tumor cell injection were well tolerated and all rats awaked after both surgeries: the tumor cells inoculation and the treatment given three days later. In all rats orthotopic tumors were successfully implanted by tumor cell injection, as was confirmed by the histological examination. It should be noticed that the Dunning R-3327 rat prostate adenocarcinoma can be induced by a number of sublines that differ in growth rate, differentiation, hormone responsiveness and metastatic ability. In our study we used the MatLyLu subline, which has the most aggressive local and metastatic potential.

Animal Model Calibration

Three groups of rats were injected with increasing concentrations of the tumor cells in their prostate gland. Because of the aggressiveness of the MatLylu subline an optimal minimal amount of cells that invoke stable but still treatable tumor was selected. As was reported earlier 18 the minimal amount of MatLyLu cells that formed tumors in all intraprostate injected animals was 5×103 cells. Following these results we used similar concentrations of cells to be convinced that tumor indeed grew in the injected prostate. On the other hand when rats were injected with 2×105 intraprostate (data not shown) the obtained tumors were huge, untreatable and all rats died within 2 weeks post cell inoculation.

Three days after tumor cell inoculation the rats were sacrificed. The prostate, lungs and liver were isolated and sent to a histopatological evaluation. Three days after tumor cell inoculation, there was an obvious tumor in the prostate gland; however, no metastases were found by macroscopic observation in all groups. The histopathology of the prostate carcinoma in the prostate of a rat three days after injection showed multiple foci of a prostate carcinoma. No metastases were found in the liver and lungs during the histological evaluation. Since all the injected amounts of tumor cells (8×103, 1.5×104 and 2.5×104) successfully caused tumor after three days it was decided to inject 8×103 tumor cells and treat the animals three days later.

Survival and Weight Loss

In intraprostatic instillation of cancer cells tumors formed very fast and were fatal in all rats. The survival of the rats is shown in Table 7.

TABLE 7

| Group | Formulation | Median survival [days] (range) | Pulmonary metastasis | Liver metastasis |
|---|---|---|---|---|
| 1 | No treatment | 24(21-25) | 4/4 | 4/4 |
| 2 | Paclitaxel/Pluronic F68 | 25 | 4/4 | 4/4 |
| 3 | P(SA:RA)2:8 + 10% paclitaxel | 32.2(21-35) | 0/5 | 0/5 |
| 4 | Paclitaxel in Ethanol 50%-Chremophor EL50% diluted in saline | 17(9-25) | 2/4 | 2/4 |

The shortest survival of the rats was in the group treated with the parenteral formulation of paclitaxel-50% of the treated animals died after the second dose, nine days post tumor cells inoculation. These rats also lost weight during the experiment (FIG. 11) which implies that their mortality and morbidity was caused by the systemic toxicity of the drug formulation. The longest survival was in group treated intratumorally with 200 μl of the polymer loaded with 10% w/w paclitaxel. Only one rat died three weeks post tumor cells inoculation, while all the other rats survived till the end of the study −35 days post tumor cell inoculation. In the non treatment group, one rat died three weeks post tumor cells inoculation and all the others three days later (day 25th after the tumor cells inoculation). Intratumoral injection of the paclitaxel/Pluronic suspension did not caused systemic toxicity, because after the intratumoral injection paclitaxel aggregated in the injection site. On the other hand this formulation did not prolong the lifetime of the rats-all rats died 25 days post tumor cells inoculation.

At autopsy all animals having large tumors (>3 cm in diameter) showed marked internal bleeding, either due to invasion of the tumor into major blood vessels or to rupture of the highly vascularized primary tumor. On the other hand rats in the polymer/paclitaxel treatment group died 10 days later then others, while having relatively small tumor. We believe that their death was caused by ureteral obstruction, because neither metastases, nor internal bleeding was seen at autopsy. From the weight loss curve it is obvious that all rats lost their weight in the first five days (FIG. 12). This weight lost was probably caused by the surgery and trauma that rats were exposed to. Starting from day five rats from all treatment groups, except the parenteral treatment with paclitaxel IP, started gaining their weight with no statistical difference between these groups. Only the systemic treatment caused statistically significant weight loss—from 231 gm to 203 gm and 50% "premature" death cases.

Lymph Node, Pulmonary and Liver Metastasis

At autopsy, lymph node metastasis was palpable and visible in tumor bearing animals (Table 8).

TABLE 8

Summary of Median Survival Rates and Pulmonary and Liver Metastasis

| Group | Formulation | Median survival [days] (range) | Pulmonary metastasis | Liver metastasis |
|---|---|---|---|---|
| 1 | No treatment | 24(21-25) | 4/4 | 4/4 |
| 2 | Paclitaxel/Pluronic F68 | 25 | 4/4 | 4/4 |
| 3 | P(SA:RA)2:8 + 10% paclitaxel | 32.2(21-35) | 0/5 | 0/5 |
| 4 | Paclitaxel in Ethanol 50%-Chremophor EL50% diluted in saline | 17(9-25) | 2/4 | 2/4 |

The rats had gross pelvic and retroperitoneal nodal involvement with a node size up to 0.6 cm. As shown in Table 8 all untreated animals and animals injected intratumorally with paclitaxel suspension shown metastases in lungs and liver. Rats that were treated with parenteral formulation of paclitaxel and died 9 days post tumor cells inoculation didn't develop metastases (probably because they died very soon) but other two rats developed metastases in lungs and liver. None metastases were found in rats treated intratumorally with 200 μl of polymer/paclitaxel formulation.

Tumor Volumes

FIG. 12 shows the volume of the prostate with the tumor in different treatment groups. In the no treatment group 1 rat died after 21 days post tumor cells inoculation having prostate volume of 11.83 $cm^3$ and other rats died on 25th days having prostate volume of 14.8±1.08 $cm^3$. In the group treated with parenteral paclitaxel the death was bimodal: half of the rats died after 9 days having prostate volume of 14.18 $cm^3$ and other rats died after 25 days having prostate volume of 13.65±0.26 $cm^3$. Better results were in the group treated with paclitaxel suspension injected intratumorally: all rats died after 25 days having prostate volume of 6.6±0.7 $cm^3$. The best results were obtained for the polymer/paclitaxel treatment where 1 rat died after 21 day having prostate volume of 0.845 $cm^3$ and other rats survived the longest period of time and died after 35 days having prostate volume of 0.862±0.16 $cm^3$, while the volume of a healthy prostate gland injected with 200 μl of polymer is about 0.4 $cm^3$.

A comparison of the prostate glands taken at day 35 from the polymer/paclitaxel group and at day 25 from all other groups clearly showed the macroscopic differences between the groups.

Histopathological Evaluations

Although all above mentioned parameters were evaluated, the only parameter that demonstrated differences among the groups was the intratumoral necrosis. All other evaluated parameters did not show any difference among the groups, as therefore this data is not presented. In the no treatment group the percent of total intratumoral necrosis was low (10-20%). In the group treated with the paclitaxel suspension the percent of total intratumoral necrosis were similar (10-15%) and only one tumor showed higher necrosis –50%. In the group treated with the parenteral formulation of paclitaxel suspension no intratumoral necrosis was found, while the highest percent of total intratumoral necrosis was found in the group treated with polymer loaded with 10% paclitaxel (25-70%). Additionally, 3 rats from the polymer/paclitaxel group were sacrificed 10 days post tumor cell inoculation and their prostate glands were sent to histopathological evaluation. Multiple areas of interstitial and intra-glandular necrosis, as well as acute inflammation were observed. However, there was no apparent presence of prostate cancer.

Metastases were found in liver and lungs in all untreated rats (group #1, 4 of 4), in all rats treated intratumorally with paclitaxel suspension (group 2, 4 of 4), in all rats treated with the parenteral formulation and none metastasis were found in rats treated with 200 μl of polymer/paclitaxel formulation.

It should be emphasized that our findings (i.e., significant difference in the amount of intra-tumoral necrosis among the groups) is consistent with what is reported in the literature with the same model exposed to estramustine and etoposid.

We have previously described the effective use of biocompatible, biodegradable and injectable polymeric gels for site directed delivery of antineoplastic drugs such as paclitaxel. The polymeric gel formulation used in this study is a viscous paste at room temperature that may be injected through a small gauge needle (23G) and it solidifies in vivo in 1 hour. This gel forms a controlled-release implant that releases the drug locally at the site of injection. In vivo studies showed that paclitaxel is released over 3-4 weeks and the implant is totally degraded during this period.

The Dunning rat MatLyLu prostatic carcinoma is analogous to hormone-refractory, metastatic human prostate cancer in many ways. Although tumors induced at ectopic sites are easily accessible for experimental manipulation, such tumors do not correspond with their anatomic origins. It is known that cancer cells outside their natural milieu behave quite differently from they do in their organ of origin.

In this study we evaluated the efficacy of the intratumoral injection of paclitaxel containing polymer in Dunning model. Orthotopic model enables us to treat cancer in its own environment as it happens in the real life. This animal model may reflect a potential treatment method for patients with recurrent prostate cancer. The therapeutic effect of paclitaxel/polymer formulation resulted from the induction of apoptosis in MatLyLu tumor cells that was documented in vitro and in vivo. We used the MatLyLu subline, which is the most aggressive and highly metastatic subline among the Dunning prostate cancer models. After calibration of this model we found an optimal amount of tumor cells to generate a homogeneously growing orthotopic tumor that can be treated. Our results show that one intratumoral administration of 200 μl of polymer/paclitaxel formulation was able to reduce the tumor growth of the MatLyLu cell Dunning prostate cancer of the Copenhagen rat in a significant manner in comparison to the control groups or systemic therapy. Treatment with paclitaxel suspension intratumorally also reduced somewhat the tumor volume, but not as good as the polymer/paclitaxel formulation and did not prolong the lifespan of the animals. After intratumoral injection of the suspension the water is eliminated and only paclitaxel powder is left in the injection site. This powder forms a cake (as was seen at autopsy of the rats). As much paclitaxel dissolves from this cake is enough to cause some necrosis at the surroundings, but not enough to prevent at all tumor progression and metastases. On the other hand, when the same volume of the polymeric formulation with 10% w/w paclitaxel was injected into the tumor, the polymer stays for weeks in the injection site. The formulation degrades and releases paclitaxel from the implant surface that is quite large. While all the prostate gland is filled with the formulation the tumor progression and metastasis formation is stopped. Thus, the best treatment is intratumoral injection of 200 μl of polymer/paclitaxel formulation. This treatment prolonged the lifespan of the rats by ten days, the tumor volume was 18 times smaller than others, the necrosis rate in the tumor tissue was significantly higher and no metastases were found.

In advanced human prostatic carcinoma without adjuvant systemic therapy, surgery to remove the prostate does little if anything to prolong survival. The current lack of an efficient adjuvant treatment emphasizes the necessity of enhancing surgery with new experimental treatment modalities. Use of injectable biodegradable paste that releases locally anti-cancer drug may solve this problem.

Example 5

Effect of Additives on Drug Release

The aim of this study was to further reduce the viscosity and to improve injectability of poly(SA:RA) (3:7)-paclitaxel formulation by incorporating ricinoleic acid, phospholipid, PEG 400 and PEG 2000 in the polymer-drug formulation without affecting the paclitaxel release from the formulation. Formulations were prepared by direct mixing of all components at room temperature, that occurred at three steps: a) Paclitaxel (5 and 10% w/w) was mixed by triruration with the additive (PEG or phospholipid); b) ricinoleic acid (20% w/w) was added to the mix; c) the mix was incorporated in p(SA:RA) (30:70) polymer paste by trituration. The composition was mixed until a smooth paste was formed. Formulations without paclitaxel were prepared by the same scheme starting at step 2. The following formulations were prepared: a) p(SA:RA) 3:7+20% ricinoleic acid (RA) containing paclitaxel (5% and 110% w/w) or without paclitaxel; b) p(SA:RA) (3:7)+20% ricinoleic acid (RA)+5% phospholipid (PL) containing paclitaxel (5% and 10% w/w) or without paclitaxel; c) p(SA:RA) 3:7+20% ricinoleic acid (RA)+5% poly(ethylene glycol) 400 (PEG 400) containing paclitaxel (5% and 110% w/w) or without paclitaxel; d) p(SA:RA) 3:7+20% ricinoleic acid (RA)+5% poly(ethylene glycol) 2000 (PEG 2000) containing paclitaxel (5% and 10% w/w) or without paclitaxel; and as a control p(SA:RA) 3:7 without additives containing paclitaxel (5% and 10% w/w) or without the drug. All formulations were prepared and filled in syringes at room temperature without further heating. The obtained formulations were semi-solid pastes at room temperature that can be injected. In vitro drug release studies were conducted by injecting 10 mg of the pasty formulation sample in a 50 ml of phosphate buffer solution (0.1 M, pH 7.4) at 37° C. with constant shaking (100 RPM). The paste hardens to soft solid shortly after addition to the buffer. The release medium was replaced periodically with fresh buffer solution and the drug concentration in the solution was determined by HPLC. All experiments were performed in triplicate.

In Vitro Hydrolytic Degradation

The in vitro hydrolysis was evaluated by injecting 25 mg of the blank polymer or pasty formulation with additives containing paclitaxel (5 and 10%, w/w) phosphate buffer solution (50 ml, 0.1 M, pH 7.4) at 37° C. with constant shaking (100 RPM). The medium was replaced periodically with fresh buffer solution. At each time point, the polymer sample was taken out of the buffer, weighed wet and dry after lyophilization. The hydrolysis of the polymer was monitored by weight loss of the sample.

Results

The selected additives to be added to the polymer P(SA:RA) (3:7) were ricinoleic acid, egg phospholipid, PEG 400 and PEG2000. These additives blended homogeneously with the polymer, and formulations with additives loaded with paclitaxel (5% and 10% w/w) could be easily injected via a 22G needle without heating.

Gel permeation chromatography (GPC) was used to determine the molecular weights of P(SA:RA) (3:7) before and after the addition of 20% w/w ricinoleic acid. After addition of 20% w/w ricinoleic acid to the polymer, the polymer molecular weight remained unchanged and the ricinoleic acid peak is seen after 8 minutes that corresponds to its molecular weight (300 g/mole). IR spectroscopy showed no change in the peak corresponding to an anhydride bond (1817 cm$^{-1}$) upon addition of the additives and/or paclitaxel.

Addition of 20% ricinoleic acid to a polymer P(SA:RA) (3:7) caused the formulation to become softer and allowed injection of the formulation containing 5% and 10% paclitaxel via 22G needle at room temperature without additional heating. Paclitaxel was dispersed in the polymer to obtain a homogenous formulation.

Example 7

Release of Peptides and Proteins

Numerous peptide and protein therapeutics have been approved or are in advanced stages of clinical testing. Extensive investigations have been carried out on polymers for controlled release systems for peptides and proteins. Most of this work has focused on PLGA. Unfortunately, bulk degradation of PLGA creates an acidic core, which can damage pH sensitive drugs such as peptides and proteins. Surface eroding polymers, such as polyanhydrides, lessen the effect of acidic build-up by increased diffusion rates of soluble fragments away from the particle. The liquid and pasty polymers described herein were used for the delivery of peptides and proteins. The advantage of using a drug delivery system of pasty state is the ease in drug incorporation by simple mixing of the drug powder in the polymer paste at room temperature without any organic solvent, heat or shear forces.

The following peptides and proteins were used in this study: leuprolide (1270 Da), octreotide (1019 Da), bovine serum albumin (BSA) (68000 Da), insulin (5860 Da), interleukin (53000 Da) and interferon alpha-2a (IFN-alpha) (19000 Da) were used. The peptides were obtained from commercial sources: leuprolide and octreotide (Novetide Ltd.), insulin (Protein Delivery Inc.), bovine serum albumin (Intergen company) interferon alpha-2a (Roferon A®, F. Hoffmann-La Roche Ltd, Basel, Switzerland), interleukin (Proleukin®, Chiron B. V., Amsterdam, Niderlands) and Folin-Ciocalteu's phenol reagent (Sigma-Aldrich) were used in this study.

LHRH and octreotide concentrations in buffer solutions were determined by an HPLC (Hewlett Packard, Waldbronn, Germany) system composed of an HP 1100 pump, HP 1050 UV detector and HP ChemStation data analysis program using a C18 reverse-phase column (LichroCart® 250-4, Lichrospher® 100, 5 μm). LHRH was eluted by acetonitrile: TEAP buffer (pH 3, 0.01M) 3:7 v/v and detected at λ=278 nm. Octreotide was eluted by acetonitrile: PBS (pH 7.4 0.02 M) and detected at λ=218 nm. BSA, insulin, IFN-alpha and interferon concentrations in buffer solutions were determined by the Lowry protein assay.

The peptides and the proteins were grinded separately in a mortar at room temperature to a fine powder. The drug powder was mixed with p(SA:RA) 2:8 or 3:7 till a homogeneous paste was achieved. In order to study the peptide release from the polymers, samples of 20 mg of p(SA:RA) (2:8) loaded with 10% w/w leuprolide and octreotide and samples of blank polymer of the same weight were prepared. The samples were incubated in 15 ml buffer phosphate solution pH 7.4, 0.1 M at 37° C., with orbital shaking (100 RPM). Samples of 2 ml were taken and analyzed by HPLC. The buffer solution was replaced every 48 hours to avoid peptide saturation and turbidity of the solution. The degradation of polymers under physiological conditions was followed by weight loss and GPC analysis for 40 days.

Protein release from the polymers: samples of 50 mg of p(SA:RA) (2:8) loaded with 10% w/w of BSA and samples of 50 mg of p(SA:RA) (3:7) loaded with 5% w/w of insulin were prepared and incubated in 20 ml of buffer; and samples of 20 mg of p(SA:RA) (3:7) loaded with 5% of interleukin and samples of 20 mg of p(SA:RA) (3:7) loaded with 5% of IFN-alpha were prepared and incubated in 10 ml of buffer. Samples of 0.2 ml were taken from the medium each 48 hours, incubated with Folin-Ciocalteu's reagent according to the Lowry assay method and analyzed with a UV spectrophotometer. The buffer solution was replaced every 48 hours to avoid protein saturation and turbidity of the solution. The results are shown in FIG. 13.

The polymers that were chosen for this study were p(SA:RA)s with 2:8 and 3:7 w/w ratios with an average molecular weight of 12,000 and 18,000, respectively. The polymers represented two IR anhydride peaks at 1732 cm$^{-1}$ and 1817 cm$^{-1}$. The peak at 1732 cm$^{-1}$ may be also referenced to the ester bonds. No free acid peaks were present at 1700 cm$^{-1}$ (C=O) and 3500 cm$^{-1}$ (O—H). NMR spectroscopy confirmed the insertion of all the RA into the PSA chain by disappearance of CH—OH peak at 3.613 ppm and appearance of CH—O—CO peak at 4.853 ppm.

The hydrolytic degradation of p(SA:RA) (2:8) loaded with 10% LHRH and octreotide was studied by weight loss and change in molecular weight. There was no significant difference in the molecular weight loss between blank and peptide polymers. The LHRH and octreotide were released constantly from the gelled polymer for over 40 days as monitored by HPLC.

Example 8

Liquid Polymer for the Delivery of Bupivacaine Local Anesthetic

Postoperative pain is considered a major problem for the patient and the healing process after surgery. Current methods, which include multiple injections of short acting local anesthetic solutions, are time-consuming and demand expensive equipment and close monitoring. Less invasive methods are generally less efficacious. This lack of efficient treatment for postoperative pain highlights the urgent need for new therapeutic principles in this area. An alternative approach is the local administration of high doses of local anesthetic agents, which can prolong the effect of the local anesthetic agents for a period of a few days or even weeks via a controlled release injectable implant. Such a site-directed drug delivery system may provide effective dose of the drug and may avoid the systemic toxicities associated with the repeated use of the systemic formulations.

Preparation of the Implant and In Vitro Drug Release

Bupivacaine free base (5, 7, 10% w/w) was incorporated in the liquid polymers by mixing the drug powder in the polymer at 40° C. and filling 1 ml syringe with this formulation. This formulation is a semi-solid at room temperature and liquid at body temperature. In vitro drug release studies were conducted by injecting 100 mg of the semi-solid formulation in a 50 ml of dissolution medium (phosphate buffer (0.1M, pH 7.4) at 37° C. with constant shaking (100 RPM). In order to simulate the in vivo sink condition a large volume of dissolution medium was used so the concentration of bupivacaine never reached more than 10% of its maximum solubility. The releasing medium was replaced periodically with fresh buffer solution and the drug concentration in the solution was determined by HPLC. All experiments were done in triplicates. Similarly, bupivacaine hydrochloride was incorporated in the polymer using similar procedure. The free base bupivacaine formed a clear solution in the polymer while the HCl salt was a fine dispersion.

Animals

Female ICR mice weighing 40 g were used. The mice were housed ten to a cage with free access to food and water. The animal room was light-cycled (12 hr light, 12 hr dark), and the temperature was 22° C. The animals were anesthetized with halothane (1.5-2%) during the identification of the sciatic nerve and the injection of the formulation. The nerve was identified with a nerve stimulator (Stimuplex® 22G diameter, B. Braun Melsungen AG, Germany. Each animal received a single injection (0.1 ml) of a bupivacaine (10% w/w) containing polymer on one side and the corresponding blank polymer or saline solution on the contralateral side.

Toxicity and Elimination of Polymer Formulations

Post-mortem histology evaluations for inflammation, infection and necrosis in the major organ, and the sciatic nerves treated with polymer-drug and controls were performed. After completion of an experiment on bupivacaine efficacy the animal was anesthetized with chloral hydrate 4% (0.2 ml), the blood was withdrawn from the heart and after the animal was sacrificed by pulmonary puncture, the major organs (heart, lungs, liver, spleen, brain, and right and left sciatic nerves) were excised and placed in a 10% formaldehyde solution for fixation. The tissue was then embedded in paraffin and stained with hematoxylin-eosin. Histological evaluation was performed by light microscopy with the assistance of the pathologists at the Animal House in the Hebrew University Hadassah Hospital. Bupivacaine concentrations in the mice blood were determined according to known procedures. Briefly, 0.5 ml mouse plasma was extracted with 1.5 ml of heptane-ethyl acetate (9:1, v/v) and shaken for 2 min. After centrifugation at 1200 g for 10 min, the organic phase was transferred into a conical tube. The second extraction step was carried out after the addition 100 μl of 0.05M sulphuric acid and shaking for 2 min. After centrifugation at 1200 g for 5 min, the organic phase was discarded and to the 50 μl of the aqueous acid base 100 μl of DDW was added. A-100 μl aliquot was injected into the chromatograph. The chromatographic system consisted of an HP 1100 pump, HP 1050 UV detector, and HP ChemStation data analysis program equipped with C18 reverse-phase column (LichroCart® 250-4, Lichrospher® 100, 5 μm). The mobile phase was a pH 2.1 mixture of acetonitrile and 0.01M sodium dihydrogenphosphate. The flow rate was 1 ml/min and UV detection was at 205 nm (injection volume 100l, run time 12 min).

Efficacy Studies In Vivo

Motor Block

The mice were assessed with regards to motor block according to a 4-point scale: 1—normal, 2—intact dorsiflexion of foot with impaired ability to splay toes when elevated by the tail, 3-toes and foot plantar flexed with no splaying ability, 4-loss of dorsiflexion, flexion of toes, and impairment of gait.

Hargreaves Hot Plate Sensory Test

This model enables independent motor and sensory testing. The mice were positioned to stand on a plate. After acclimatization to the apparatus, an infrared beam (standard heat temperature 50-52° C.) is directed at the tested hind paw. Latency to withdraw the hind paw from the hot plate is recorded by alternating paws and allowing at least 15 sec. recovery between plate measurements. Because the withdrawal muscles for the leg are thigh adductors (femoral not sciatic nerve) the mice can withdraw a paw despite total (level 4) sciatic nerve block. In addition, a pinprick is applied to the foot, and a reaction (yes=1, or no=0) will be recorded.

Statistical Analysis

The Hargreves (time to event) scores were analyzed using a mixed model analysis of variance. The main question of interest was whether drug affected Hargreves score. Two experiments were conducted, and different animals were used at various times. Drug, experiment, and hour were considered as fixed effects, and animal (nested within experiment and hour) was considered to be a random effect. SAS Proc Mixed (Version 8.02) was used to perform the analyses.

Results

In Vitro Drug Release

Bupivacaine was incorporated in the polymer without affecting the polymer molecular weight, as confirmed by GPC. Bupivacaine free base (BFB) is easily soluble in P(SA-RA) up to 15% w/w BFB. The hydrochloride salt dispersed well in the polymer without affecting its viscosity at least up to 15% w/w loading. P(SA-RA) 2:8 and 3:7 formulations containing 5% and 7% of bupivacaine constantly released the drug at a first order profile with about 60% of the incorporated drug was released during 7 days in buffer, formulation containing 10% released approximately 70% of its content during this period. For all experiments, the higher MW polymers (Mw=18,000) release the drug at a slower rate, between 10 and 20% less the amount released at each time point, compared to the low MW polymers (Mw=5,000).

Toxicity and Histopathological Evaluation

The histological evaluation of the sciatic nerves, the surrounding tissues (fat and muscle) and the major organs was performed on mice sacrificed three days and one week post the injection. Three days post the injection only in one mouse out of three was macrophage infiltration found in the fat surrounding the sciatic nerve. In the other two mice the right and the left nerve, the surrounding muscle and fat were found normal. All the other examined organs (lung, liver, heart, brain and spleen) were found normal in all the examined mice. In the histological examination performed one week post injection only in two mice out of five rare neutrophils and perineural lymphocytes were found in the tissue surrounding the sciatic nerve, and all the examined organs (lung, liver, heart, brain and spleen) were found normal in all the examined mice.

The plasma concentration of bupivacaine after the injection of 10 mg of the drug loaded in the polymer was studied. After 24 hours the plasma level reached 75±15 ng/ml, and then dropped to 18±5 ng/ml after 6 days and after day 7 to day 21 the plasma levels were almost undetectable (7±2 ng/ml). These plasma concentrations did not cause any observed systemic toxicity, like convulsions, and all mice that received 10 mg of bupivacaine loaded in the polymer survived the study.

Efficacy

Hargreaves Hot Plate Sensory Test was performed during 4 days post injection of the bupivacaine formulation. It was found that the anesthesia effect was maintained during 3 days post injection. The motor block disappeared 24-36 hours post injection.

Conclusions: Based on these results poly(sebacic-co-ricinoleic acid) delays the bupivacaine release and prolongs the anasthesia without any negative pathological effect.

Example 9

Poly(Sebacic-co-Ricinoleic-Ester-Anhydride) Biodegradable Carrier for Controlled Release of Gentamicin for the Treatment of Osteoporosis Osteomyelitis is a bone infection usually caused by bacteria but sometimes by a fungus. There are three possible ways by which bone can be infected. Bone infection can be caused by the extension of infection from adjacent soft tissue that has been injured or has poor blood circulation. Infections from other parts of the body can be carried to the bones through the blood (hematogenous spread). Direct bone infection can be the result of a penetrating wound or open fracture. The treatment of bone infection mainly involves operative debridement, removal of all foreign bodies, and antibiotic therapy. Usually, intravenous antibiotics are prescribed for 3 weeks, followed by 3 weeks of oral antibiotics. However, the high parenteral dose of antibiotic required to achieve effective therapeutic drug levels in the bone as well as the prolonged course of treatment can lead to systemic toxicity of the anti biotic. Local delivery of antibiotics to the infected site offers major advantages over traditional intravenous therapy. A local drug delivery system can achieve a high drug concentration at the site of infection while maintaining low systemic drug levels. Drug delivery systems developed for local delivery of antibiotics can be divided into non biodegradable and biodegradable carriers. Polymethylmethacrylate (PMMA) beads containing gentamicin have been approved for use in treatment of osteomyelitis in Europe. Although this product has been proven to be efficacious, it suffers from the major drawback of being non-biodegradable and requiring subsequent removal of the beads at the completion of antibiotic release. In recent years, various biodegradable delivery systems have been developed and evaluated for local delivery of antibiotics in the treatment of bone infections. Gentamicin sulfate, a potent antibiotic agent, is currently used for treatment of osteomyelitis mainly by intravenous injection with a long-term indwelling catheter, local implant of antibiotic containing polymethylmethacrylate beads or calcium phosphate (bone cements).

In Vitro Gentamicin Release

P(SA:RA) (3:7) w/w ratio polymers with different molecular weights were prepared as described in Example 1. Gentamicin sulfate was mixed in poly(SA:RA) 3:7 at room temperature without any heating or use of solvent until a homogenous mixture was obtained. Drug loadings were 10% and 20%. Drug release studies were conducted by placing 200 mg of the formulation in 50 ml phosphate buffer (0.1 M, pH 7.4) at 37° C. with constant shaking (100 rpm). To simulate the flow of biological fluids, the buffer solution was replaced every 48 hours and the replaced solutions were kept for gentamicin analysis.

For the in vitro release assay, 25 μl of the formulation was placed at the bottom of each well in a 24-well microtitre flat bottom plate (available from Nonc, Copenhagen, Denmark). On ml of phosphate buffer saline (PBS) was added and the plate were incubated in humid chamber at 37° C. At each time point, the dissolution medium was collected, the formulation was washed with one ml of PBS and a fresh one ml of PBS was added to the wells. The medium was centrifuged and the supernatant was kept for the bacterial study and gentamicin concentration analysis.

The collected samples were diluted 100 times, reacted with fluorescamine (Sigma, Israel) and analyzed by a spectrofluorometer (Jasco, Japan) at an excitation wavelength of 392 nm and an emission wavelength of 480 nm to determine gentamicin concentration.

The formulation prepared for this study contained 20-40 mg of gentamicin. Gentamicin loaded polymers were prepared by simple mixing of the drug powder in the polymer paste. No chemical interactions between the drug salt and the polymer were observed. The rate of gentamicin release from the pasty polymers into buffer phosphate is shown in FIG. 14. It can be seen that formulations with 20% gentamicin have slower release profiles than that of formulations with 10% gentamicin. This difference in the release profile is most likely due to salt formation between gentamicin and the fatty degradation products of the polymer. In both cases, increasing the molecular weight of the polymer decreases the gentamicin release rate. Gentamicin loaded polymers with Mn>10,000 Da were viscous and difficult to inject. Therefore P(SA-RA) 3:7 (Mn=4500) loaded with 20% gentamicin was chosen for further investigation.

In a second in vitro release study, gentamicin was released into a 24-well tray (1 ml solution/well). The formulations used in this study contained approximately 5 mg of active gentamicin. The release profile was similar to the release profile obtained when releasing in a large volume of water. For example, after eight days, 9% (about 0.45 mg) of the loaded gentamicin was released. The overall results indicate a constant release of gentamicin over an extended period of time (e.g. greater than 60 days) which is an advantage for treatment of chronic infections or for prevention of a recurrent infection. The antimicrobial activity of the released gentamicin in the buffer solution was confirmed by over night incubation with S. aureus in TSB and determining the viability of the bacteria.

In Vitro Antibacterial Activity

The supernatant solutions from the in vitro release study of polymers containing gentamicin was added to cultures of S. aureus. The collected supernatant was diluted 100 times, 1000 times and 10000 times with PBS and added to the wells in a 96 well microtitre flat bottom plate that contained $10^6$ S. aureus in TSB. The plate was incubated inside a temperature controlled microplate spectrophotometer (VERSAmax, Molecular Devices Corporation, CA<USA) for 24 hours. Optical density (OD) measurements were performed every two hours at 650 nm to determine the bacterial concentration in the wells. A correlation was found between gentamicin concentration determined by the fluorescamine method and the bacterial effect in vitro.

The minimum inhibitory concentration of gentamicin for the S. aureus used in this study is 2-4 μg/ml. The results of the VERSAmax spectrophotometer analysis are summarized in FIG. 15. After 6 and 8 days the gentamicin concentration was sufficient to eradicate S. aureus when the solutions were diluted 100 (4.5×10-3 mg/ml) and 1,000 (4.5×$10^{-4}$ mg/ml) times, respectively (A and B in FIG. 15). In the case of 10,000 time dilution (C in FIG. 15) the concentration was not inhibitory. The control wells with the blank P(SA-RA) (3:7) w/w (Mn=4500) did not affect the growth of bacteria. No effect was found in these wells: the O.D. was approximately 0.7. In the wells that contained S. aureus in TSB only, O.D. of approximately 0.6 was found. In view of the results of gentamicin release (FIG. 14) and the profound bacterial inhibition by the diluted solutions (FIG. 15), there is probably a significant antibacterial activity in the release medium at an earlier stage.

In Vivo Efficacy and Drug Concentration in the Injection Site

Injectable p(sebacic-co-ricinoleic-ester-anhydride) 3:7 and 2:8 w/w polymers loaded with 10 and 20% gentamicin sulfate were used. Efficacy studies were performed on rats infected with Staphylococcus aureus (S. aureus) in both proximal tibia of 16 mail Wistar rats. The legs were shaved, depilated and disinfected with alcohol. To provide sterile conditions during the surgery, the animals were placed on sterile drapes and the bodies were covered with sterile sheets. The legs were draped separately with a sterile incision foil. The skin and fascia at the proximal tibial methaphysis were incised over 5 mm in length. A hole was drilled (titanium burr 3 mm) through the cortical and cancellous bone. A suspension of *S. aureus* containing $1.0 \times 10^6$ colony forming units (CFUs) per ml was prepared. Ten μl of the suspension was injected with a 50 μl syringe into each wound site. The animal was maintained for 4 weeks to allow osteomyeliis to develop. After this period, radiographs of the affected limbs were made and the rats underwent treatment. The formulation was injected into the infected bone of the rats from the test group.

The test group received p(SA:RA) injections. 100 μl of the polymer loaded with 10% gentamicin was injected via a 23G needle into the infected bone. The control group did not receive any treatment.

After killing the animals, the limbs were disarticulated at the wrist and elbow. Radiographs of each specimen were taken. Two mm tissue samples were taken from the implantation sites after 1, 2, 4, and 8 weeks. The tissue was homogenized in 1 ml of normal saline (pH 7.4) and centrifuged. Supernatant was removed and analyzed by a Fluorescence Polarization Immunoassay (FPIA), which is available from Abbott Diagnstics under the tradename TDx, to determine gentamicin concentration.

In all animals, a significant reduction in bacteria count WAS found compared to the control groups. Gentamicin was found in the analyzed tissues after 4 weeks and traces amount were observed after 8 weeks.

Toxicity of Polymer-Gentamicin Implant

Male Wistar rats, 10 week old (Harlan laboratories, Jerusalem, Israel) were kept under specific pathogen free conditions and given free access to irradiated food and acidified water throughout the experiment. The ethics committee at the Hebrew University of Jerusalem (National Institutes of Health approval number: OPRR-A01-5011) has reviewed the application for animal study and found it compatible with the standards for care and use of laboratory animals (ethics committee research number: MD-80.04-3).

200 μl of gentamicin-loaded semi-solid formulation (0%, 10% and 20% w/w) were injected subcutaneously in the front of the abdomen of two groups of three Wistar rates via a 19G needle. One group was implanted with a formulation containing 200 μl of p(SA:RA) (3:7) blank on the left side and 200 μl of p(SA:RA) (3:7) loaded with 20% gentamicin on the right side. The second group was implanted with a formulation containing 200 μl of p(SA:RA) (3:7) blank on the left side and 200 μl of p(SA:RA) (3:7) loaded with 10% gentamicin on the right side. The animals were observed for local toxicity signs and for weight loss. Six weeks after injection the rats were sacrificed, the implant was removed for chemical analysis and the surrounding tissue was fixed in 4% neutrally buffered formaldehyde and subjected to histopathological examination.

Histopathological evaluation indicated that in the samples taken from the 2 groups in which 10% or 20% gentamicin formulation was added to the polymer p(SA:RA) (3:7), the degree of capsular tissue reaction was comparable to that formed when the blank polymer alone was present, suggesting no adverse reaction upon application of the combined therapeutic modality. The formed capsule was predominantly composed of mature collagen deposition, associated with the presence of fibroblasts, blood vessels and sparse histiocytes or other mononuclear cells. No evidence of any active inflammatory reaction or tissue irritation was present within the capsule or extending beyond the local capsule. In all cases the thicknesses of the capsules were similar. The local tissue reaction typically consisting of a thin enveloping capsule was interpreted as a scarring subchronic inflammatory reaction. No evidence of granulomatous foreign-body, lymphoid cell aggregation, and/or immunological stimulation was noted, indicating that the implants were well tolerated.

The biocompatibility of the polymer (poly(RA-SA) (70:30) and the 20% gentamicin loaded formulation with bone was determined by drilling holes in the rat tibia and injecting into the bone 0.2 ml of the polymer or formulation. Groups of 5 rats were used in this study. The bones were analyzed histopathologically and no evidence of toxicity attributed to the polymer or formulation was found. The inflammation noted in response to the polymer was consistent with active removal of the material via normal mechanisms. The polymer and formulation were completely eliminated from bone after 8 weeks post implantation.

Stability to γ-Irradiation

P(SA:RA) (3:7) w/w with 20% gentamicin sulfate (GS) was used in this study. After the polymerization was complete, GS was added to the pasty polymer at room temperature and mechanically mixed till a homogeneous mixture was achieved. One ml of the mixture was loaded into 1 ml lock plastic syringes. Syringes containing one ml of blank polymer were also prepared. All polymers were irradiated with an absorbed dose of 2.5 Mrad by means of a $^{60}$Co source (450 000 Ci; 8 h). The irradiation was conducted at Sor-Van Radiation Ltd. (Kiryat Soreq, Yavne, Israel).

The molecular weights of the loaded and blank polymers before and after the irradiation were measured by GPC. The melting points of the loaded and blank polymers before and after the irradiation were measured by DSC. The chemical structures of the loaded and blank polymers before and after the irradiation were determined by IR and $^1$H-NMR spectroscopy. Gentamicin content was determined by dissolving samples before and after irradiation in dichloromethane and extracting the drug with doubly distilled water (DDW) three times. The extracts were combined and analyzed using a spectrafluorometer.

After irradiation the formulations were stored at 37° C., 20° C., 4° C. and −17° C. Non-irradiated samples were used as control. At different time points, the samples were withdrawn from the irradiated and control formulations and analyzed by the methods described above. The results are shown in Table 9.

TABLE 9

Changes in molecular weights (Mn and Mw) and melting points (m.p.) of stored polymers.

| Storage conditions | Sampling | Mn (Da)$^a$ | | | m.p. (C.)$^b$ |
| --- | --- | --- | --- | --- | --- |
| | | Irradiated formulation | Non-irradiated formulation | Irradiated blank polymer | |
| 37° C. | 0 day | 5000 | 5000 | 5000 | 32 |
| | 1 day | 4000 | 4200 | 5000 | 32 |
| | 3 days | 2000 | 2000 | 2500 | 30 |
| | 7 days | 2000 | 2100 | 2000 | 30 |
| | 10 days | 1700 | 1700 | 1600 | 27 |
| | 14 days | 1300 | 1200 | 1300 | 27 |
| 20° C. | 0 day | 5000 | 5000 | 5000 | 32 |
| | 1 day | 5000 | 5000 | 5000 | 32 |
| | 7 days | 5000 | 5000 | 5000 | 32 |
| | 14 days | 4000 | 3900 | 4100 | 32 |
| | 21 days | 4000 | 4000 | 4200 | 32 |
| | 28 days | 3500 | 3200 | 3000 | 31 |
| | 35 days | 2100 | 2000 | 2200 | 31 |
| | 42 days | 1700 | 1800 | 1600 | 29 |
| | 49 days | 1700 | 1500 | 1400 | 28 |
| | 56 days | 1500 | 1500 | 1400 | 28 |

TABLE 9-continued

Changes in molecular weights (Mn and Mw) and melting points (m.p.) of stored polymers.

| Storage conditions | Sampling | Mn (Da)[a] | | | m.p. (C.)[b] |
| --- | --- | --- | --- | --- | --- |
| | | Irradiated formulation | Non-irradiated formulation | Irradiated blank polymer | |
| 4° C. | 0 days | 5000 | 5000 | 5000 | 32 |
| | 28 days | 5000 | 5000 | 5000 | 32 |
| | 56 days | 3700 | 3500 | 4100 | 32 |
| | 100 days | 2000 | 2000 | 2000 | 29 |
| −17° C. | 0 days | 5000 | 5000 | 5000 | 32 |
| | 56 days | 5000 | 5000 | 5000 | 32 |
| | 100 days | 5000 | 5000 | 5000 | 32 |
| | 150 days | 5000 | 5000 | 5000 | 32 |
| | 200 days | 5000 | 5000 | 5000 | 32 |

[a]The weight-average molecular weight (Mw) and number-average molecular weight (Mn) were determined by GPC.
[b]Melting point (m.p.) was recorded by DSC at 10° C./min for irradiated samples only.

At some points, a brief drug release study was conducted in order to detect possible changes in drug release due to the storage conditions. The release profiles of the formulations stored at 4° C. and −17° C. are shown in FIG. 16. The release of gentimicin was similar in the two formulations. The samples were dissolved in dichloromethane and extracted three time with phosphate buffer (0.1 M, pH=7.4). FIG. 16a shows the release of gentimicin from a formulation stored at 4° C. for 8 weeks. FIG. 16b shows the release of gentimicin from a formulation stored at −17° C. for 8 weeks. The release profiles of the irradiated and non-irradiated samples were similar indicating that irradiation did not release of the drug from the polymer effect of irradiation. Storage at room temperature for two weeks did not appear to affect the release profile of gentamicin. There was no difference between IR and NMR spectra for the irradiated and non-irradiated formulations. Degradation during storage can be followed by IR spectroscopy by monitoring the disappearance of the anhydride peak and the appearance of acid peak at 1700 $cm^{-1}$. No degradation was indicated for the formulations stored at −17° C. The formulations that were stored at 4° C. developed an acid peak after six weeks which increased with time.

Example 9

Liquid Polyesters Containing Ricinoleic Acid Oligomers

Ricinoleic acid oligomers of Mw=2200 and 3600 prepared by direct condensation of ricinoleic acid were used in this study. Hydroxy terminated RA oligomers were obtained by reacting the RA oligomers with ethylene oxide or propylene oxide which formed the ester of ethylene glycol or propylene glycol. The hydroxyl terminated RA oligomers were used as initiators for the ring opening polymerixation of DL-lactide, caprolactone and glycolic acid and their mixtures. ABA triblock copolymers with B segment being ricinoleic acid oligomer were obtained by ring opening polymerization of HO terminated RA oligomers with DL-lactide using staneous octoate as catalyst. The molar ratio between the RA oligomer and lactide determined the polymer molecular weight and segment length. Triblock copolymers of DL-lactide containing 20% RA oligomers were liquid at room temperature and form a gel in water. Similarly, pasty polymers were obtained from diblock copolymers of DL-lactide and RA oligomers having one hydroxyl group.

Random copolymers of RA oligomers and hydroxyl acids were obtained by polycondensation of ricinoleic acid oligomers with lactic acid, glycolic acid, and hydroxyl butyric acid. The polymerization is taking place in toluene with acidic catalysis. After toluene evaporation, the polymerization continues at 130° C. under 1 mm Hg vacuum to yield a pasty polymer at a less than 10% lactic acid content. Various copolymers were obtained from the copolymerization of hydroxyl acids and their lactones into polyesters. These polymers increase in viscosity when injected in the body and release an incorporated drug for weeks and months, depending mainly on the water solubility of the drug.

Example 10

Synthesis and Characterization of Polyesters of Ricinoleic Acid with Lactic and Glycolic Acid L-lactic acid (50% solution in water) was lyophilized over night before use. Castor oil and L-Lactic acid with w/w ratios 1:10, 1:5, 2:5, 3:5 (w/w castor oil to lactide) were mixed with 0.5% w/w $H_3PO_4$ as catalyst and heated to 170° C. under a stream of dry $N_2$ for 1.5 hours to dry the system. After 1.5 hours, the reaction was connected to a vacuum of 15 mBar and the reaction was continued for 24 hours. Samples were taken at 3, 5 and 7 hours of polymerization.

The appearance and the weight average and number average molecular weights of the polymers are described in Table 4. Polyesters of Ricinoleic Acid and Lactic acid were also prepared. The properties of these polymers are described in Table 5. Copolymerization of lactic acid with ricinoleic acid/castor oil resulted in polymers with desired properties such as pliability, hydrophobicity and softness. The presence of ricinoleic acid in the polymer chains resulted in steric hindrance of the polymer to yield soft or even liquid polymers. These pasty polymers gelled to a harder material when immersing the polymer in aqueous solution. Injection of these polymeric pastes into tissue resulted in localization of the polymer formulation at the site of injection.

TABLE 10

Properties of Polyesters of Castor Oil and Lactic Acid

| Castor oil/l-lactide w/w ratio | 3 h | | 5 h | | 7 h | | 24 h | | |
| --- | --- | --- | --- | --- | --- | --- | --- | --- | --- |
| | Mn/Mw | appearance | Mn/Mw | appearance | Mn/Mw | appearance | Mn/Mw | appearance | m.p |
| 10:90 | Mn = 402 Mw = 1454 | Liquid | Mn = 2877 Mw = 3307 | Liquid | Mn = 2825 Mw = 4267 | solid | Mn = 4301 Mw = 6767 | Solid brittle | 115° C. |
| 20:80 | Mn = 981 Mw = 2004 | Liquid | Mn = 3046 Mw = 3701 | Liquid | Mn = 3756 Mw = 5207 | solid | Mn = 6944 Mw = 13996 | Solid pasty | 75° C. |
| 30:70 | Mn = 2294 Mw = 2534 | Liquid | Mn = 2677 Mw = 3133 | Liquid | Mn = 3148 Mw = 4104 | pasty | Mn = 6567 Mw = 10558 | Liquid | Liquid at R.T |

TABLE 11

Properties of Polyesters of Ricinoleic Acid and Lactic Acid

| Ricinoleic acid/lactide w/w ratio | 24 h | |
|---|---|---|
| | Mn/Mw | appearance |
| 20:80 | Mn = 4510<br>Mw = 10945 | Solid brittle |
| 30:70 | Mn = 4126<br>Mw = 10103 | paste |
| 40:60 | Mn = 4393<br>Mw = 10509 | Liquid at RT |

Polymers containing 30:70 ratio w/w (30% castor oil or ricinoleic acid) were synthesized from DL-Lactic acid and glycolic acid and mixtures thereof. All polymers showed a similar molecular weight of Mn in the range of 4000 and were pasty materials. The DL-lactic acid polymer was more liquid-like than the other polymers. All polymers change their viscosity and gel when placed in aqueous media for one hour at room temperature.

Example 11

In Vitro Release of Taxol and Methotrexate from Polyesters of Ricinoleic Acid and Lactic Acid Formulations containing 10% w/w taxol and 10% w/w/ methotrexate were prepared by mixing the drug with the poly(lactic acid:castor oil) 60:40 and 70:30 w/w ratio copolymers having a Mn=3,000 and Mw=7,000. The drug was mixed with the polymer at room temperature using a mortar and pestle. No solvents or heat were used. The particle size of the drug particles in the pasty formulation was less than 100 microns as determined by SEM analysis.

A 1 mL syringe was filled with the drug-polymer formulation and samples of 10 mg each were injected into 50 ml phosphate buffer having a pH of 7.4 at 37° C. The buffer solution also contained 0.3% w/v sodium dodecyl sulfate (SDS). SDS was added to increase the solubility of the released paclitaxel. The buffer was replaced daily during the first week and every 3 days afterwards. The release of paclitaxel and methotrexate was monitored by HPLC. Taxol and Methotrexate were released at a constant rate from the polymer formulation with the polymer remaining as uniform semi-solid droplets without disintegration. 25% of the loaded Methotrexate was released at a constant rate for about 20 days while 5% and 10% of the loaded paclitaxel was released for after about 30 and 60 days, respectively.

I claim:

1. A hydrophobic polymer composition comprising a polyester or a poly(ester-anhydride) composed of ricinoleic acid ester oligomer units and units of aliphatic molecules having at least one carboxylic acid and at least one hydroxyl group or one additional carboxylic acid group, the composition being a liquid or a paste at a temperature below 37° C. and forming a gel in aqueous solution.

2. The composition of claim 1, wherein said poly(ester-anhydride) comprises alkanedioic acid monomer units having at least 4 carbon atoms.

3. The composition of claim 2, wherein said alkanedioic acid monomer units are selected from the group consisting of linear dicarboxylic acid of the structure $HOOC(CH_2)_xCOOH$ where x is an integer between 2 and 16, fumaric acid and maleic acid.

4. The composition of claim 3, wherein said alkanedioic acid is sebacic acid.

5. The composition of claim 4, wherein said poly(ester-anhydride) is composed of ricinoleic acid ester oligomer units and monomer units of sebacic acid.

6. The composition of claim 1, wherein said polyester or said poly(ester-anhydride) comprises one or more hydroxyalkanoic acid monomer units having from 2 to 6 carbon atoms.

7. The composition of claim 6, wherein the hydroxyalkanoic acid monomer units are selected from the group consisting of lactic acid, glycolic acid, 4-hydroxybutanoic acid, and 5-hydroxypentanoic acid.

8. The composition of claim 1, wherein said ricinoleic acid ester oligomer units have at least an average of 1.5 ricinoleic acid units linked by an ester bond.

9. The composition of claim 1, further comprising one or more excipients.

10. The composition of claim 1, wherein said polyester or poly(ester-anhydride) has a weight-average molecular weight of 10,000 Da or higher.

11. The composition of claim 1, where said polyester or poly(ester-anhydride) has a degree of polymerization of 40 or higher.

12. The composition of claim 1, wherein said polyester or poly(ester-anhydride) biodegrades in about 12 weeks.

13. The composition of claim 1, further comprising at least one active agent.

14. The composition of claim 13, wherein said active agent is selected from the group consisting of therapeutic, diagnostic, and prophylactic agents.

15. The composition of claim 14, wherein said active agent is selected from the group consisting of small drug molecules, peptides, proteins, oligo and polynucleotides, herbicides, and pesticides.

16. The composition of claim 14, wherein said active agent is selected from the group consisting of analgesics, local anesthetics, anti-infectives, antinflammatory agents, antibiotics, growth hormones, anticancer agents, and combinations thereof.

17. The composition of claim 13, wherein said at least one active agent comprises an anticancer agent, the composition being identified for use in treating solid tumors.

18. The composition of claim 13, wherein said at least one active agent comprises an agent selected from the group consisting of an ant-infective agent, an antibiotic, and an antiviral agent, the composition being identified for use in treating a bone infection and/or a soft tissue infection.

19. The composition of claim 1, being identified for use as a surgical sealant.

20. The composition of claim 1, being identified for use as a barrier for reduction of organ to organ adhesion.

21. The composition of claim 1, being identified for use as a coating.

22. The composition of claim 21, wherein said composition is applied as a coating of a medical device.

23. The composition of claim 1, being identified for use by injection or implantation thereof.

* * * * *

UNITED STATES PATENT AND TRADEMARK OFFICE
CERTIFICATE OF CORRECTION

| | |
|---|---|
| PATENT NO. | : 8,575,092 B2 |
| APPLICATION NO. | : 11/992669 |
| DATED | : November 5, 2013 |
| INVENTOR(S) | : Domb |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1305 days.

Signed and Sealed this
Twenty-sixth Day of May, 2015

Michelle K. Lee
*Director of the United States Patent and Trademark Office*